(12) United States Patent
Engel

(10) Patent No.: US 8,273,716 B2
(45) Date of Patent: *Sep. 25, 2012

(54) USE OF LHRH ANTAGONISTS FOR INTERMITTENT TREATMENTS

(75) Inventor: Juergen Engel, Alzenau (DE)

(73) Assignee: Spectrum Pharmaceuticals, Inc., Irvine, CA (US)

( * ) Notice: Subject to any disclaimer, the term of this patent is extended or adjusted under 35 U.S.C. 154(b) by 677 days.

This patent is subject to a terminal disclaimer.

(21) Appl. No.: 12/394,374

(22) Filed: Feb. 27, 2009

(65) Prior Publication Data

US 2009/0221569 A1 Sep. 3, 2009

Related U.S. Application Data

(60) Provisional application No. 61/032,447, filed on Feb. 29, 2008.

(30) Foreign Application Priority Data

Feb. 29, 2008 (EP) .................................... 08102143

(51) Int. Cl.
*A61K 38/06* (2006.01)
*A61P 35/00* (2006.01)
*C07D 209/82* (2006.01)

(52) U.S. Cl. ....... 514/21.9; 530/331; 514/19.5; 548/439

(58) Field of Classification Search .................. None
See application file for complete search history.

(56) References Cited

U.S. PATENT DOCUMENTS

| 5,663,145 | A | 9/1997 | Engel et al. |
| 8,067,456 | B2 * | 11/2011 | Paulini et al. .................. 514/411 |
| 2006/0014818 | A1 | 1/2006 | Paulini et al. |
| 2008/0032935 | A1 | 2/2008 | Engel et al. |
| 2008/0280965 | A1 | 11/2008 | Paulini et al. |

| 2009/0018177 | A1 | 1/2009 | Hirano et al. |
| 2009/0075937 | A1 | 3/2009 | Engel et al. |
| 2009/0170783 | A1 | 7/2009 | Schuster et al. |
| 2009/0181964 | A1 | 7/2009 | Hirano et al. |

FOREIGN PATENT DOCUMENTS

| EP | 1 752 452 A1 | 2/2007 |
| EP | 1 864 976 A1 | 12/2007 |
| EP | 1 967 202 A1 | 9/2008 |
| EP | 1 988 098 A1 | 11/2008 |
| WO | WO 96/03138 A1 | 2/1996 |
| WO | WO 98/10781 * | 3/1998 |
| WO | WO 02/102401 A1 | 12/2002 |
| WO | WO 03/011314 A2 | 2/2003 |
| WO | WO 03/011314 A3 | 2/2003 |

OTHER PUBLICATIONS

International Search Report issued on Aug. 5, 2009 in corresponding International Application No. PCT/EP2009/052326 filed on Feb. 27, 2009.

Zhiqiang Guo et al., "Uracils as Potent Antagonists of the Human Gonadotropin-Releasing Hormone Receptor Without Atropisomers", Bioorganic & Medical Chemistry Letters, May 16, 2005, vol. 15, No. 10, XP 025314320, pp. 2519-2522.

Chen Chen, et al., "Discovery of Sodium*R*-(+)-4-(2-[5-(2-Fluoro-3-methoxyphenyl)-3-(2-fluoro-6-[trifluoromethyl]-benzyl)-4-methyl-2,6-dioxo-3,6-dihydro-2*H*-pyrimidin-1-yl]-1-phenylethylamino) butyrate (Elagolix), a Potent and Orally Available Nonpeptide Antagonist of the Human Gonadotrophin-Releasing Hormone Receptor", Journal of Medicinal Chemistry, 2008, vol. 51, No. 23, XP 002538508, pp. 7478-7485.

* cited by examiner

*Primary Examiner* — Karlheinz R Skowronek
*Assistant Examiner* — Satyanarayana R Gudibande
(74) *Attorney, Agent, or Firm* — K&L Gates LLP; Louis C. Cullman; Dean G. Stathakis

(57) ABSTRACT

The invention relates to methods of treatment or prophylaxis of physiological and/or pathological conditions with at least one LHRH antagonist, in particular at least one peptidomimetic LHRH antagonist such that the at least one LHRH antagonist is administered in a dose, which does not cause chemical (hormonal) castration.

28 Claims, No Drawings

USE OF LHRH ANTAGONISTS FOR INTERMITTENT TREATMENTS

CROSS-REFERENCE TO RELATED APPLICATIONS

This application claims the benefit of EP 08102143,08 and U.S. 61/032,447 both filed Feb. 29, 2008, each of which is incorporated herein by reference.

DESCRIPTION

1. Field of the Invention

The invention relates to medicaments comprising LHRH antagonists for use in the treatment or prophylaxis of physiological and/or pathological conditions such as prostate cancer, benign prostate hyperplasia (BPH) and endometriosis. The invention further relates to the treatment or prophylaxis of above symptoms by administering LHRH antagonists in intermediate doses, which do not cause chemical (hormonal) castration.

2. Background of the Invention

G-protein coupled receptors represent a superfamily of cell membrane-associated receptors which play an important part in numerous biochemical and pathobiochemical processes in mammals and especially in humans. All GPCRs consist of seven hydrophobic, transmembrane alpha-helical domains which are connected together by three intracellular and three extracellular loops and have an extracellular amino terminus and an intracellular carboxy terminus. One or more heterotrimeric G proteins are involved in their cellular signal transduction. Diverse physiological stimuli such as photosensitivity, taste and odor, but also fundamental processes such as metabolism, reproduction and development are mediated and controlled by them. GPCRs exist for exogenous and endogenous ligands. Peptide hormones, biogenic amines, amino acids, nucleotides, lipids, $Ca^{2+}$, but also photons, have inter alia been identified as ligands; moreover one ligand may activate different receptors.

According to a recent investigation, 367 sequences have been identified in the human genome for G-protein coupled receptors (GPCRs) with endogenous ligands (Vassilatis D K et al., PNAS 2003, 100(8): 4903-4908). Of these, 284 belong to class A, 50 to class B, 17 to class C and 11 to class F/S. Examples belonging to class A are the bombesin, the dopamine and the LHRH receptors, and to class B are the VIP and the calcitonin receptors. The natural ligands for numerous GPCRs are as yet unknown.

Owing to their function, GPCRs are suitable as targets for medicaments for the therapy and prevention of a large number of pathological conditions. It is speculated that about 50% of currently known targets for active ingredients are GPCRs (Fang Y et al., DDT 2003, 8(16): 755-761). Thus, GPCRs play an important part in pathological processes such as, for example, pain (opioid receptor), asthma (beta2-adrenoceptor), migraine (serotonin 5-HT1B/1D receptor), cancer (LHRH receptor), cardiovascular disorders (angiotensin receptor), metabolic disorders (GHS receptor) or depression (serotonin 5-HT$_{1a}$ receptor) (Pierce K L et al., Nat. Rev. Mol. Cell Biol. 2002, 3: 639-650). General information about GPCRs is to be found under http://www.gpcr.org.

The natural ligand of this receptor, the peptide hormone LHRH, is synthesized in cells of the hypothalamus and released in pulsatile fashion from the hypothalamic neurons into the capillary plexus of the ementia mediana. In the anterior lobe of the pituitary, LHRH binds to the LHRH receptors of the gonadotropic cells and stimulates certain trimeric G-proteins, which initiate a branched signal transduction cascade. The initial event is activation of phospholipase C, $A_2$ and/or D. This leads to an increased provision of the second messengers diacylglycerol and $IP_3$, followed by $Ca^{2+}$ mobilization from intracellular pools, and activation of various subordinate protein kinases. Finally, there is stimulation of the production and temporally defined pulsatile release of the gonadotropins FSH and LH. The two hormones are transported via the circulation to the target organs the testes and ovaries respectively. There they stimulate the production and release of the appropriate sex hormones. In the opposite direction there is a complex feedback mechanism by which the concentration of the sex hormones formed in turn regulates the release of LH and FSH.

In the male organism, LH binds to membrane receptors of the Leydig cells and stimulates testosterone biosynthesis. FSH acts via specific receptors on the Sertoli cells and assists the production of spermatozoa. In the female organism, LH binds to the LH receptors of the theca cells and activates the formation of androgen-synthesizing enzymes. FSH stimulates proliferation of granulosa cells of certain follicle stages via the FSH receptors thereof. The androgens which are formed are converted in the adjacent granulosa cells to the estrogens estrone and estradiol.

A number of disorders distinguished by benign or malignant tissue proliferations depend on stimulation by sex hormones such as testosterone or estradiol. Typical disorders of this type are prostate cancer and benign prostate hyperplasia (BPH) in men, and endometriosis, uterine fibroids or uterine myomas, pubertas praecox, hirsutism and polycystic ovary syndrome, and breast cancer, uterine cancer, endometrial cancer, cervical cancer and ovarian cancer in women.

Since its discovery in 1971 by Schally et al. (Schally A et al., Science 1971, 173: 1036-1038) more than 3000 synthetic analogues of natural LHRH have been synthesized and tested. Peptide agonists such as triptorelin and leuprolide have been established for many years successfully in the therapy of gynecological disorders and cancers. However, the disadvantage of agonists is generally that they stimulate LHRH receptors in the initial phase of use and thus lead to side effects via an initial increase in the sex hormone levels. Only after downregulation of the LHRH receptor as a result of this overstimulation can the superagonists display their effect. This leads to a complete reduction in the sex hormone levels and thus to pharmacological castration with all the signs and symptoms. This disadvantage is associated with the impossibility of targeted adjustment of the level of sex hormones via the dosage. Thus, therapy of diseases which do not require a total reduction of the sex hormone levels to the castration level, such as, for example, benign tissue proliferations, with an agonist is not optimal for the patient.

This has led to the development of peptide LHRH receptor antagonists, of which, for example, cetrorelix (Cetrotide®) has been successfully introduced for controlled ovarian stimulation in the context of the treatment of female infertility. The antagonists inhibit the LHRH receptor immediately and dose-dependently, and thus lead to an immediate reduction in the plasma levels of testosterone or estradiol and progesterone. The peptide antagonists are, however, somewhat less potent than the agonists, and thus higher doses must be given.

Reviews of the clinical applications and the potential of LHRH agonists and antagonists are given by Millar R P et al. (Millar R P et al., British Med. Bull. 2000, 56: 761-772), Felberbaum R E et al. (Felberbaum R E et al., Mol. Cell. Endocrinology 2000, 166: 9-14) and Haviv F et al. (Haviv F et al., Integration of Pharmaceutical Discovery and Development: Case Studies, Chapter 7, ed. Borchardt et al., Plenum Press, New York 1998).

Besides the treatment of malignant and benign neoplastic diseases, further possible applications are controlled ovarian stimulation in the context of in vitro fertilization, fertility control (contraception), and protection from unwanted side effects of radio- or chemotherapy, the treatment of HIV infections (AIDS) and of neurological or neurodegenerative disorders such as Alzheimer's disease. Specific LHRH receptors have not only been found on pituitary cells, but also on cells in various tumors, e.g. of the breast and ovaries. These receptors might mediate a direct antiproliferative effect of LHRH receptor antagonists on the tumor.

The peptide LHRH receptor agonists and antagonists are mostly decapeptides whose bioavailability is inadequate for oral administration. They are typically given as solutions for injection or as depot formulation, subcutaneously or intramuscularly. This application is associated with inconveniences for the patient, and the compliance suffers. In addition, synthesis of the decapeptides is complicated and costly.

Compared with peptide LHRH receptor agonists and antagonists, as yet no non-peptide compound is approved and in clinical use for any of the possible indications. The current state of development in the area of LHRH receptor agonists and antagonists is described in the reviews by Zhu Y F et al., Expert Opin. Therap. Patents 2004, 14(2): 187-199, Zhu Y F et al., Ann. Rep. Med. Chem. 2004, 39: 99-110, Tucci F C et al., Curr. Opin. Drug Discovery & Development 2004, 7(6): 832-847, Armer R E, Curr. Med. Chem. 2004, 11: 3017-3028, Chengalvala M V et al., Curr. Med. Chem-Anti-Cancer Agents 2003, 3: 399-410. The former publication contains a comprehensive list of the published patent specifications describing the synthesis and use of low molecular weight LHRH receptor antagonists.

Among the first examples of non-peptide LHRH receptor antagonists is the 4-oxothieno[2,3-b]pyridine structure, which was described by Cho N et al. (Cho N et al., J. Med. Chem. 1998, 41: 4190-4195). Although these compounds, such as, for example, T-98475, have a high receptor affinity, their solubility in water is very poor and their bioavailability is low. Based on this lead structure, numerous further developments have been carried out, examples which may be mentioned being the publications of the international applications WO 95/28405, WO 96/24597, WO 97/14697 and WO 97/41126. The synthesis of thieno[2,3-d]pyrimidine-2,4-diones as orally available LHRH receptor antagonists is described by Sasaki S et al., (Sasaki S et al., J. Med. Chem. 2003, 46: 113-124).

Novel 1-arylmethyl-5-aryl-6-methyluracils are described by Guo Z et al. (Guo Z et al., J. Med. Chem. 2004, 47: 1259-1271). The preparation of N-[(hetero)arylmethyl]-benzenesulfonamides as potent non-peptide LHRH receptor antagonists is disclosed in WO 03/078398. The patent application WO 02/11732 describes tricyclic pyrrolidines as LHRH receptor antagonists. Substituted pyridin-4-ones as LHRH receptor antagonists are disclosed in WO 03/13528 and substituted 1,3,5-triazine-2,4,6-triones in WO 03/11839.

The syntheses and biological activities of erythromycin A derivatives having LHRH receptor antagonistic activity is described by Randolph J T et al. (Randolph J T et al., J. Med. Chem. 2004, 47(5): 1085-1097). Selected derivatives show an oral activity on the LH level in the castrated rats model.

Quinoline derivatives as non-peptide LHRH antagonists are disclosed for example in WO 97/14682. Substituted 2-arylindoles are described inter alia in WO 97/21435, WO 97/21703, WO 98/55116, WO 98/55470, WO 98/55479, WO 99/21553, WO 00/04013 as LHRH receptor antagonists. Correspondingly substituted aza-2-arylindoles are claimed inter alia in WO 99/51231, WO 99/51596, WO 00/53178 and WO 00/53602 as LHRH receptor antagonists. Advantageous biological or biophysical data for these compounds are not disclosed.

Patent EP 0 679 642 B1 describes fused heterocyclic compounds as LHRH receptor antagonists. However, a basic tetrahydrocarbazole structure is not the subject matter of the invention described therein.

1,2,3,4-Tetrahydrocarbazolecarboxylic acids are described in patent EP 0 239 306 B1 as prostaglandin antagonists. An LHRH receptor antagonistic effect is neither described nor obvious.

U.S. Pat. No. 3,970,757 discloses tetrahydrocarbazole derivatives as gastric anti-secretory agents. However, an LHRH receptor antagonistic effect of this type of structure is neither described nor obvious.

EP 0 603 432 B1 and U.S. Pat. No. 5,708,187 describe tetrahydrocarbazole derivatives as 5-HT1 agonists inter alia for the treatment of migraine. However, an LHRH receptor antagonistic effect is neither described nor obvious.

WO 2005/033099 A2 describes tetrahydrocarbazole derivatives as dipeptidyl peptidase IV inhibitors. However, an LHRH receptor antagonistic effect is neither described nor obvious. There is no reference to an LHRH receptor antagonistic effect, and the disclosed structures differ from the compounds of the present invention.

Davies D J et al. describe tetrahydrocarbazole derivatives having a melatonin agonistic or antagonistic effect (Davies D J et al., J. Med. Chem. 1998, 41: 451-467). However, an LHRH receptor antagonistic effect is neither described nor obvious.

Tetrahydrocarbazole derivatives are described by Shuttleworth S J et al. as partial agonists of the neuromedin B receptor (Shuttleworth S J et al., Bioorg. Med. Chem. Lett. 2004, 14: 3037-3042). However, an LHRH receptor antagonistic effect is neither described nor obvious.

Millet R et al. describe tetrahydrocarbazole derivatives as $NK_1/NK_2$ ligands. The disclosed structures differ from the compounds of the present invention (Millet R et al., Letters in Peptide Science 1999, 6: 221-233). Moreover, an LHRH receptor antagonistic effect is neither described nor obvious.

Solid-phase synthesis of 3-amino-3'-carboxytetrahydrocarbazoles described by Koppitz et al. (Koppitz et al., THL 2005, 46(6): 911-914). An LHRH receptor antagonistic effect is neither described nor obvious.

Tetrahydrocarbazole derivatives as peptidomimetic LHRH receptor antagonists having good receptor affinity are disclosed for example in WO 03/051837. The physicochemical and metabolic properties of these compounds do not, however, make them suitable in an optimal manner for an oral dosage form.

A number of publications provide an overview of the state of development of neurokinin antagonists:

Giardina G et al. provide an overview of the current patent literature (Giardina G et al., IDrugs 2003, 6(8): 758-772), Leroy V et al. (Leroy V et al., Expert Opinion on Investigational Drugs 2000, 9(4), 735-746) and Swain C et al. (Swain C et al., Annual Reports in Medicinal Chemistry 1999, 34: 51-60) describe the state of development relating to neurokinin receptor antagonists, while, for example, Navari R M et al. (Navari R M et al., Cancer Investigation 2004, 22(4): 569-576) describes the results of clinical studies in which NK1 receptor antagonists were employed to control chemotherapy-induced emesis.

Hill R G et al. describe neurokinin receptor antagonists as potential analgesics (Hill R G et al., Pain 2003, 523-530), while von Sprecher A et al. describe neurokinin receptor antagonists as potential active ingredients for the therapy of inflammations and rheumatoid arthritis (Sprecher A et al., IDrugs 1998, 1(1): 73-91). Millet R et al. describe tetrahydrocarbazole derivatives as $NK_1/NK_2$ ligands (Millet R et al., Letters in Peptide Science 1999, 6: 221-233). The disclosed structures differ from the compounds of the present invention.

WO 2006/005484 discloses tetrahydrocarbozole derivatives that are said to show improved biological action and improved solubility. These tetrahydrocarbozole derivatives act as ligands for G-protein coupled receptors, in particular LHRH receptor and NK receptors.

DESCRIPTION OF THE INVENTION

The present invention has the object to provide novel treatments for hormone-dependent diseases such as prostate cancer, benign prostate hyperplasia (BPH) and endometriosis by which negative hormone withdrawal symptoms are prevented.

The object of the present invention has been solved in one aspect by providing a medicament comprising at least one LHRH antagonist, in particular at least one pepti-domimetic LHRH antagonist, for use in the treatment or prophylaxis of physiological and/or pathological conditions selected from the group consisting of: "benign tumor diseases, malignant tumor diseases, male fertility control, hormone therapy, hormone replacement therapy, female sub- or infertility, controlled ovarian stimulation in in vitro fertilization (COS/ART), female contraception, side effects due to chemotherapy, prostate cancer, breast cancer, uterine cancer, endometrial cancer, cervical cancer, ovarian cancer, benign prostate hyperplasia (BPH), endometriosis, uterine fibroids, uterine myomas, endometrium hyperplasia, dysmenorrhoea, dysfunctional uterine bleeding (menorrhagia, metrorrhagia), pubertas praecox, hirsutism, polycystic ovary syndrome, hormone-dependent tumor diseases, HIV infections or AIDS, neurological or neurode-generative disorders, ARC (AIDS related complex), Kaposi sarcoma, tumors originating from the brain and/or nervous system and/or meninges, dementia, Alzheimer's disease, nausea, vomiting, pain, inflammations, chronic inflammations, acute inflammations, rheumatic and arthritic pathological states, chronic pain, panic disorder, disturbances of mood and sleep, depression, fibromyalgia, post-traumatic stress disorder, tension headache, migraine headache, anxiety, generalized anxiety disorder, bowel syndrome, irritable bowel sysndrome, stress-induced hypertension, asthma, emesis, cough, cystitis of the bladder, pancreatitis and/or atopic dermatitis" and preferably selected from the group consisting of: "prostate cancer, benign prostate hyperplasia (BPH), endometriosis", wherein the at least one LHRH antagonist is to be administered in an intermediate dose, which does not cause chemical (hormonal) castration.

Corresponding uses comprising at least one LHRH antagonist for the preparation of a medicament for the treatment or prophylaxis of herewithin disclosed physiological and/or pathological conditions are also comprised by the present invention.

In a preferred embodiment, a medicament comprising at least one LHRH antagonist, in particular at least one pepti-domimetic LHRH antagonist, is provided that can be used in the treatment or prophylaxis of herewithin disclosed physiological and/or pathological conditions, wherein the LHRH antagonist is selected from the group consisting of: tetrahydrocarbozole compound of the formula (I)

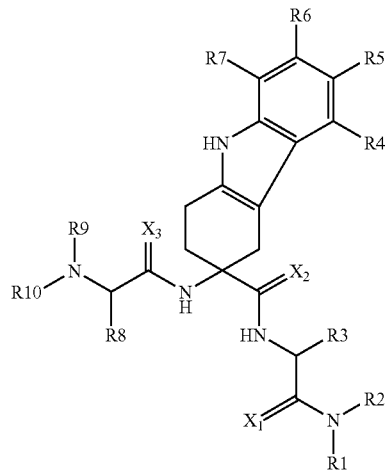

in which:

$X_1$ is S, O or $S^+$—$O^-$, $X_2$ and $X_3$ are independently of one another O or geminally linked $H_2$, R1 and R2 are independently of one another selected from the group consisting of —H, aryl, alkyl and arylalkyl radicals which are optionally substituted in the alkyl and/or aryl group by up to 3 substituents independently selected from the group consisting of Hal, —CN and —O-alkyl, where R1 and R2 are in particular hydrogen, R3 is an alkyl, arylalkyl or heteroarylalkyl radical, which are optionally substituted by up to 3 substituents independently selected from the group consisting of Hal, —CN, —CO—O—R12, —CO—NR12R12', —OH, —O—R13, —O—CO—R13, —O—SO$_2$—OR12, —O—SO$_2$—R12, —SO$_2$—OR12, —SO—R12, —O—PO(OR12)(OR12'), —O—PO(NR12R12')$_2$, —O—CO—O—R13, —O—CO—NR12R12', —O—CS—NR12R12', —S—R12, —NR12, R12', —NH—CO—R13, —NH—SO$_2$—R12, —NH—CO—O—R13, —NH—CO—NHR12, —NH—C(NH)—NH$_2$, R4, R5, R6 and R7 are selected independently of one another from the group consisting of H, Hal, —CN, —CONH$_2$, —COOH, —CF$_3$, —O-alkyl, —OCF$_3$, —NO$_2$, and alkyl, arylalkyl and heteroarylalkyl radicals;

R9 is a hydrogen atom, an alkyl, an aryl, a heteroaryl, an arylalkyl or a heteroarylalkyl radical, preferably a hydrogen atom;

R10 is a hydrogen atom, or the radical —R11, —CO—R11, —CO—OR11, —CO—NHR11, —C(NH)—NHR11, —SO$_2$—R11, or —SO$_2$—NHR11;

R11 is an alkyl, an aryl, a heteroaryl, an arylalkyl or a heteroarylalkyl radical, which are optionally substituted by one or more substituents independently selected from the group consisting of Hal, —CN, -alkyl, —CF$_3$, —OCF$_3$, —OH, —O-alkyl, and —O—(CH$_2$CH$_2$—O)$_n$—CH$_3$;

R8 is —C$_1$-C$_6$-alkyl-aryl or —C$_1$-C$_6$-alkyl-heteroaryl, where the aryl or heteroaryl group is substituted by one to three, preferably by one, substituents independently selected from the group consisting of —O—(CH$_2$CH$_2$—O)$_n$—CH$_3$, —O—CO—R12, —O—CO—(CH$_2$CH$_2$—O)$_n$—CH$_3$, —O—SO$_2$—OR12, —O—SO$_2$—R12, —O—PO (OR12)(OR12'), —O—PO(NR12R12')$_2$, —O—CO—OR13, —O—CO—NR12R12', and —O—CS—NR12 R12', or, where, however, at least
(i) X$_1$ is S, or
(ii) R10 is not H, and R11 is an arylalkyl or heteroarylalkyl radical, which are substituted in the aryl or heteroaryl group by one or more substituents independently selected from the group consisting of Hal, —CN, -alkyl, —CF$_3$, —OCF$_3$, —OH, —O—alkyl, and —O—(CH$_2$CH$_2$—O)$_n$—CH$_3$, R8 also assumes the meanings indicated for R3;

R12 and R12' are independently of one another H, or an alkyl, arylalkyl, aryl, heteroarylalkyl, or heteroaryl radical and are preferably H, R13 is selected from an alkyl, arylalkyl, aryl, heteroarylalkyl, and heteroaryl radical, or is the group —(CH$_2$CH$_2$—O)$_n$—CH$_3$, and n is an integer from 1 to 10, preferably 1 to 6.

In a preferred embodiment, a medicament comprising at least one LHRH antagonist, in particular at least one peptidomimetic LHRH antagonist, is provided that can be used in the treatment or prophylaxis of herewithin disclosed physiological and/or pathological conditions, In a further preferred embodiment, at least one LHRH antagonist, in particular at least one peptidomimetic LHRH antagonist, is provided that can be used for the preparation of a medicament for the treatment or prophylaxis of herewithin disclosed physiological and/or pathological conditions, wherein the LHRH antagonist is selected from the group consisting of:

(R)-8-chloro-6-fluoro-3-{(S)-2-[2-(2-fluorophenyl)acetylamino]-3-methylpentanoyl-amino}-2,3,4,9-tetrahydro-1H-carbazole-3-carboxylic acid ((S)-2-methyl-1-thiocarbamoylbutyl) (68), (R)-3-{(S)-2-[2-(2-fluorophenyl)acetylamino]-3-methyl-pentanoylamino}-8-trifluoro-methyl-2,3,4,9-tetrahydro-1H-carbazole-3-carboxylic acid ((S)-2-methyl-1-thio-carbamoylbutyl)amide (76), Above tetrahydrocarbazole compounds of the formula (I) and tetrahydrocarbazole compounds (68) and (77) are known from WO 2006/005484.

In a further preferred embodiment, a medicament comprising at least one LHRH antagonist, in particular at least one peptidomimetic LHRH antagonist, is provided that can be used in the treatment or prophylaxis of herewithin disclosed physiological and/or pathological conditions, wherein the LHRH antagonist is selected from the group consisting of: tetrahydrocarbazole derivative of the formula (II)

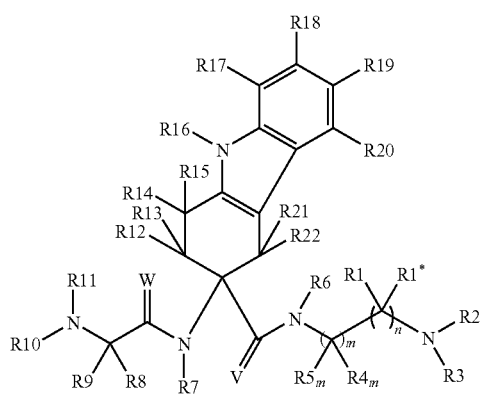

(II)

wherein:
(A) V, W are independently from each other selected from the group consisting of: "=O, =S, =S$^+$—O$^-$, geminally linked H$_2$";

R1, R1*—when present—together independently form "=O, =S or =S$^+$—O$^-$" or are independently both "hydrogen";

R2, R3 are independently from each other selected from the group consisting of:

(i) "hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHX1, —NX2X3, —NO$_2$, —OH, =O, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—X4, —C(O)O—X5, —C(O)NH—X6, —C(O)NX7X8, —O—X9, —O(—X10-O)$_a$—H (a=1, 2, 3, 4, 5), —O(—X11-O)$_b$—X12 (b=1, 2, 3, 4, 5), —OC(O)—X13, —OC(O)—O—X14, —OC(O)—NHX15, —O—C(O)—NX16X17, —OP(O)(OX18)(OX19), —OSi(X20)(X21)(X22), —OS(O$_2$)X23, —NHC(O)—NH$_2$, —NHC(O)X24, —NX25C(O)—X26, —NH—C(O)O—X27, —NH—C(O)—NH—X28, —NH—C(O)—NX29X30, —NX31-C(O)—O—X32, —NX33-C(O)—NH—X34, —NX35-C(O)—NX36X37, —NHS(O$_2$)—X38, —NX39S(O$_2$)—X40, —S—X41, —S(O)—X42, —S(O$_2$)—X43, —S(O$_2$)NH—X44, —S(O$_2$)NX45X46, —S(O$_2$)O—X47, —P(O)(OX48)(OX49), —Si(X50)(X51)(X52), —C(NH)—NH$_2$, —C(NX53)-NH$_2$, —C(NH)—NHX54, —C(NH)—NX55X56, —C(NX57)-NHX58, —C(NX59)-NX60X61, —NH—C(O)—NH—O—X62, —NH—C(O)—NX63-O—X64, —NX65-C(O)—NX66-O—X67, —N(—C(O)—NH—O—X68)$_2$, —N(—C(O)—NX69-O—X70)$_2$, —N(—C(O)—NH—O—X71)(—C(O)—NX72-O—X73), —C(S)—X74, —C(S)—O—X75, —C(S)—NH—X76, —C(S)—NX77X78, —C(O)—NH—O—X79, —C(O)—NX80-O—X81, —C(S)—NH—O—X82, —C(S)—NX83-O—X84, —C(O)—NH—NH—X85, —C(O)—NH—NX86X87, —C(O)NX88-NX89X90, —C(S)—NH—NH—X91, —C(S)—NH—NX92X93, —C(S)—NX94-NX95X96, —C(O)—C(O)—O—X97, —C(O)—C(O)—NH$_2$, —C(O)—C(O)—NHX98, —C(O)—C(O)—NX99X100, —C(S)—C(O)—O—X101, —C(O)—C(S)—O—X102, —C(S)—C(S)—O—X103, —C(S)—C(O)—NH$_2$, —C(S)—C(O)—NHX104, —C(S)—C(O)—NX105X106, —C(S)—C(S)—NH$_2$, —C(S)—C(S)—NHX107, —C(S)—C(S)—NX108X109, —C(O)—C(S)—NH$_2$, —C(O)—C(S)—NHX110, —C(O)—C(S)—NX111X112";

wherein X1, X2, X3, X4, X5, X6, X7, X8, X9, X10, X11, X12, X13, X14, X15, X16, X17, X18, X19, X20, X21, X22, X23, X24, X25, X26, X27, X28, X29, X30, X31, X32, X33, X34, X35, X36, X37, X38, X39, X40, X41, X42, X43, X44, X45, X46, X47, X48, X49, X50, X51, X52, X53, X54, X55, X56, X57, X58, X59, X60, X61, X62, X63, X64, X65, X66, X67, X68, X69, X70, X71, X72, X73, X74, X75, X76, X77, X78, X79, X80, X81, X82, X83, X84, X85, X86, X87, X88, X89, X90, X91, X92, X93, X94, X95, X96, X97, X98, X99, X100, X101, X102, X103, X104, X105, X106, X107, X108, X109, X110, X111, X112 are independently from each other selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively X7, X8 and/or X16, X17 and/or X29, X30 and/or X36, X37 and/or X45, X46 and/or X55, X56 and/or X60, X61 and/or X77, X78 and/or X86, X87 and/or X89, X90 and/or X92, X93 and/or X95, X96 and/or X99, X100 and/or X105, X106 and/or X108, X109 and/or X111, X112 and/or respectively together can also form "heterocyclyl";

wherein optionally above substituents of substituents group (i) can in turn independently from each other be substituted with at least one substituent, identical or different, selected from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —$CF_3$, —$N_3$, —$NH_2$, —NHX201, —NX202X203, —$NO_2$, —OH, =O, —$OCF_3$, —SH, —O—$SO_3$H, —OP(O)(OH)$_2$, —CHO, —COOH, —C(O)$NH_2$, —$SO_3$H, —P(O)(OH)$_2$, —C(O)—X204, —C(O)O—X205, —C(O)NH—X206, —C(O)NX207X208, —O—X209, —O(—X210-O)$_c$—H (c=1, 2, 3, 4, 5), —O(—X211-O)$_d$—X212 (d=1, 2, 3, 4, 5), —OC(O)—X213, —OC(O)O—X214, —OC(O)—NHX215, —O—C(O)NX216X217, —OP(O)(OX218)(OX219), —OSi(X220)(X221)(X222), —OS($O_2$)—X223, —NHC(O)—$NH_2$, —NHC(O)—X224, —NX225C(O)—X226, —NH—C(O)—O—X227, —NH—C(O)—NH—X228, —NH—C(O)—NX229X230, —NX231-C(O)—O—X232, —NX233-C(O)—NH—X234, —NX235-C(O)—NX236X237, —NHS($O_2$)—X238, —NX239S($O_2$)—X240, —S—X241, —S(O)—X242, —S($O_2$)—X243, —S($O_2$)NH—X244, —S($O_2$)NX245X246, —S($O_2$)O—X247, —P(O)(OX248)(OX249), —Si(X250)(X251)(X252), —C(NH)—$NH_2$, —C(NX253)-$NH_2$, —C(NH)—NHX254, —C(NH)—NX255X256, —C(NX257)-NHX258, —C(NX259)-NX260X261, —NH—C(O)NH—O—X262, —NH—C(O)NX263-O—X264, —NX265-C(O)—NX266-O—X267, —N(—C(O)—NH—O—X268)$_2$, —N(—C(O)—NX269-O—X270)$_2$, —N(—C(O)—NH—O—X271)(—C(O)—NX272-O—X273), —C(S)—X274, —C(S)—O—X275, —C(S)—NH—X276, —C(S)—NX277X278, —C(O)—NH—O—X279, —C(O)—NX280-O—X281, —C(S)—NH—O—X282, —C(S)—NX283-O—X284, —C(O)—NH—NH—X285, —C(O)—NH—NX286X287, —C(O)—NX288-NX289X290, —C(S)—NH—NH—X291, —C(S)—NH—NX292X293, —C(S)—NX294-NX295X296, —C(O)—C(O)—O—X297, —C(O)—C(O)—$NH_2$, —C(O)—C(O)—NHX298, —C(O)—C(O)—NX299X300, —C(S)—C(O)—O—X301, —C(O)—C(S)—O—X302, —C(S)—C(S)—O—X303, —C(S)—C(O)—$NH_2$, —C(S)—C(O)—NHX304, —C(S)—C(O)—NX305X306, —C(S)—C(S)—$NH_2$, —C(S)—C(S)—NHX307, —C(S)—C(S)—NX308X309, —C(O)—C(S)—$NH_2$, —C(O)—C(S)—NHX310, —C(O)—C(S)—NX311X312";

wherein X201, X202, X203, X204, X205, X206, X207, X208, X209, X210, X211, X212, X213, X214, X215, X216, X217, X218, X219, X220, X221, X222, X223, X224, X225, X226, X227, X228, X229, X230, X231, X232, X233, X234, X235, X236, X237, X238, X239, X240, X241, X242, X243, X244, X245, X246, X247, X248, X249, X250, X251, X252, X253, X254, X255, X256, X257, X258, X259, X260, X261, X262, X263, X264, X265, X266, X267, X268, X269, X270, X271, X272, X273, X274, X275, X276, X277, X278, X279, X280, X281, X282, X283, X284, X285, X286, X287, X288, X289, X290, X291, X292, X293, X294, X295, X296, X297, X298, X299, X300, X301, X302, X303, X304, X305, X306, X307, X308, X309, X310, X311, X312 are independently from each other selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively X207, X208 and/or X216, X217 and/or X229, X230 and/or X236, X237 and/or X245, X246 and/or X255, X256 and/or X260, X261 and/or X277, X278 and/or X286, X287 and/or X289, X290 and/or X292, X293 and/or X295, X296 and/or X299, X300 and/or X305, X306 and/or X308, X309 and/or X311, X312 and/or respectively together can also form "heterocyclyl";

wherein optionally above substituents of substituents group (ii) can in turn independently from each other be substituted with at least one substituent, identical or different, selected from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —$CF_3$, —$N_3$, —$NH_2$, —NHX401, —NX402X403, —$NO_2$, —OH, =O, —$OCF_3$, —SH, —O—$SO_3$H, —OP(O)(OH)$_2$, —CHO, —COOH, —C(O)$NH_2$, —$SO_3$H, —P(O)(OH)$_2$, —C(O)—X404, —C(O)O—X405, —C(O)NH—X406, —C(O)NX407X408, —O—X409, —O(—X410-O)$_e$—H(e=1, 2, 3, 4, 5), —O(—X411-O)$_f$—X412 (f=1, 2, 3, 4, 5), —OC(O)—X413, —OC(O—O—X414, —OC(O)—NHX415, —O—C(O)—NX416X417, —OP(O)(OX418)(OX419), —OSi(X420)(X421)(X422), —OS($O_2$)—X423, —NHC(O)—$NH_2$, —NHC(O)—X424, —NX425C(O)—X426, —NH—C(O)—O—X427, —NH—C(O)—NH—X428, —NH—C(O)—NX429X430, —NX431-C(O)—O—X432, —NX433-C(O)—NH—X434, —NX435-C(O)—NX436X437, —NHS($O_2$)—X438, —NX439S($O_2$)—X440, —S—X441, —S(O)—X442, —S($O_2$)X443, —S($O_2$)NH—X444, —S($O_2$)NX445X446, —S($O_2$)O—X447, —P(O)(OX448)(OX449), —Si(X450)(X451)(X452), —C(NH)—$NH_2$, —C(NX453)-$NH_2$, —C(NH)—NHX454, —C(NH)—NX455X456, —C(NX457)-NHX458, —C(NX459)-NX460X461, —NH—C(O)—NH—O—X462, —NH—C(O)—NX463-O—X464, —NX465-C(O)—NX466-O—X467, —N(—C(O)—NH—O—X468)$_2$, —N(—C(O)—NX469-O—X470)$_2$, —N(—C(O)—NH—O—X471)(—C(O)—NX472-O—X473), —C(S)—X474, —C(S)—O—X475, —C(S)—NH—X476, —C(S)—NX477X478, —C(O)—NH—O—X479, —C(O)—NX480-O—X481, —C(S)—NH—O—X482, —C(S)—NX483-O—X484, —C(O)—NH—NH—X485, —C(O)—NH—NX486X487, —C(O)—NX488-NX489X490, —C(S)—NH—NH—X491, —C(S)—NH—NX492X493, —C(S)—NX494-NX495X496, —C(O)—C(O)—O—X497, —C(O)—C(O)—$NH_2$, —C(O)—C(O)—NHX498, —C(O)—C(O)—NX499X500, —C(S)—C(O)—O—X501, —C(O)—C(S)O—X502, —C(S)—C(S)—O—X503, —C(S)—C(O)—$NH_2$, —C(S)—C(O)NHX504, —C(S)—C(O)—NX505X506, —C(S)—C(S)—$NH_2$, —C(S)—C(S)—NHX507, —C(S)—C(S)—NX508X509, —C(O)—C(S)—$NH_2$, —C(O)—C(S)—NHX510, —C(O)—C(S)—NX511X512";

wherein X401, X402, X403, X404, X405, X406, X407, X408, X409, X410, X411, X412, X413, X414, X415, X416, X417, X418, X419, X420, X421, X422, X423, X424, X425, X426, X427, X428, X429, X430, X431, X432, X433, X434, X435, X436, X437, X438, X439, X440, X441, X442, X443, X444, X445, X446, X447, X448, X449, X450, X451, X452, X453, X454, X455, X456, X457, X458, X459, X460, X461, X462, X463, X464, X465, X466, X467, X468, X469, X470, X471, X472, X473, X474, X475, X476, X477, X478, X479, X480, X481, X482, X483, X484, X485, X486, X487, X488, X489, X490, X491, X492, X493, X494, X495, X496, X497, X498, X499, X500, X501, X502, X503, X504, X505, X506, X507, X508, X509, X510, X511, X512 are independently from each other selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and wherein alternatively X407, X408 and/or X416, X417 and/or X429, X430 and/or X436, X437 and/or X445, X446 and/or X455, X456 and/or X460, X461 and/or X477, X478 and/or X486, X487 and/or X489, X490 and/or X492, X493 and/or X495, X496 and/or X499, X500 and/or X505, X506 and/or X508, X509 and/or X511, X512 and/or respectively together can also form "heterocyclyl";

n independently is 0 or 1;

with the first proviso that, if R1, R1* are not present (n is 0), R2, R3 must not both be "hydrogen" at the same time;

with the second proviso that, if R1, R1* are present (n is 1) and together independently form "=O, =S or =S⁺—O⁻" or are independently both "hydrogen", R2, R3 must not both be "hydrogen" at the same time;

with the third proviso that, if R1, R1* are not present (n is 0), one of R2, R3 must not be "hydrogen" at the same time when the other one of R2, R3 is "—C(=NH)—NH₂";

with the fourth proviso that, if R1, R1* are present (n is 1) and are independently both "hydrogen", one of R2, R3 must not be "hydrogen" at the same time when the other one of R2, R3 is "—C(=NH)—NH₂";

with the fifth proviso that, if R1, R1* are present (n is 1) and together independently form "=O" and one of R2, R3 independently is "hydrogen" and the other one of R2, R3 independently is "alkyl, cycloalkyl, cycloalkylalkyl, aryl, arylalkyl, heteroaryl", then the other one of R2, R3 being "alkyl, cycloalkyl, cycloalkylalkyl, aryl, arylalkyl, heteroaryl" must be substituted with at least one substituent selected from the group consisting of:

(iv) "heterocyclyl, heterocyclylalkyl, —CF₃, —N₃, —NH₂, —NHX600, —NX601X602, —NO₂, —OH, —OCF₃, —SH, —O—SO₃H, —OP(O)(OH)₂, —CHO, —COOH, —SO₃H, —P(O)(OH)₂, —C(O)—X603, —C(O)O—X604, —C(O)NH—X605, —C(O)NX606X607, —O-aryl, —O-arylalkyl, —O-heteroaryl, —O—heteroarylalkyl, —O-heterocyclyl, —O-heterocyclylalkyl, —O(—X608-O)_g—H (g=1, 2, 3, 4, 5), —O(—X609-O)_h—X610 (h=1, 2, 3, 4, 5), —OC(O)—X611, —OC(O)—O—X612, —OC(O)—NHX613, —O—C(O)—NX614X615, —OP(O)(OX616)(OX617), —OSi(X618)(X619)(X620), —OS(O₂)X621, —NHC(O)—X622, —NX623C(O)—X624, —NH—C(O)—O—X625, —NH—C(O)—NH—X626, —NH—C(O)—NX627X628, —NX629-C(O)—O—X630, —NX631-C(O)—NH—X632, —NX633-C(O)—NX634X635, —NHS(O₂)—X636, —NX637S(O₂)—X638, —S—X639, —S(O)—X640, —S(O₂)X641, —S(O₂)NH—X642, —S(O₂)NX643X644, —S(O₂)O—X645, —P(O)(OX646)(OX647), —Si(X648)(X649)(X650), —C(NH)—NH₂, —C(NX651)-NH₂, —C(NH)—NHX652, —C(NH)—NX653X654, —C(NX655)-NHX656, —C(NX657)-NX658X659, —NH—C(O)—NH—O—X660, —NH—C(O)NX661-O—X662, —NX663-C(O)—NX664-O—X665, —N(—C(O)—NH—O—X666)₂, —N(—C(O)—NX667-O—X668)₂, —N(—C(O)—NH—O—X669)(—C(O)—NX670-O—X671), —C(S)—X672, —C(S)—O—X673, —C(S)—NH—X674, —C(S)—NX675X676, —C(O)—NH—O—X677, —C(O)—NX678-O—X679, —C(S)—NH—O—X680, —C(S)—NX681-O—X682, —C(O)—NH—NH—X683, —C(O)—NH—NX684X685, —C(O)—NX686-NX687X688, —C(S)—NH—NH—X689, —C(S)—NH—NX690X691, —C(S)—NX692-NX693X694, —C(O)—C(O)—O—X695, —C(O)—C(O)—NH₂, —C(O)—C(O)—NHX696, —C(O)—C(O)—NX697X698, —C(S)—C(O)—O—X699, —C(O)—C(S)—O—X700, —C(S)—C(S)—O—X701, —C(S)—C(O)—NH₂, —C(S)—C(O)—NHX702, —C(S)—C(O)—NX703X704, —C(S)—C(S)—NH₂, —C(S)—C(S)—NHX705, —C(S)—C(S)—NX706X707, —C(O)—C(S)—NH₂, —C(O)—C(S)—NHX708, —C(O)—C(S)—NX709X710";

wherein X600, X601, X602, X603, X604, X605, X606, X607, X608, X609, X610, X611, X612, X613, X614, X615, X616, X617, X618, X619, X620, X621, X622, X623, X624, X625, X626, X627, X628, X629, X630, X631, X632, X633, X634, X635, X636, X637, X638, X639, X640, X641, X642, X643, X644, X645, X646, X647, X648, X649, X650, X651, X652, X653, X654, X655, X656, X657, X658, X659, X660, X661, X662, X663, X664, X665, X666, X667, X668, X669, X670, X671, X672, X673, X674, X675, X676, X677, X678, X679, X680, X681, X682, X683, X684, X685, X686, X687, X688, X689, X690, X691, X692, X693, X694, X695, X696, X697, X698, X699, X700, X701, X702, X703, X704, X705, X706, X707, X708, X709, X710, X711, X712 are independently from each other selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and wherein alternatively X606, X607 and/or X614, X615 and/or X627, X628 and/or X634, X635 and/or X643, X644 and/or X653, X654 and/or X658, X659 and/or X675, X676 and/or X684, X685 and/or X687, X688 and/or X690, X691 and/or X693, X694 and/or X697, X698 and/or X703, X704 and/or X706, X707 and/or X709, X710 and/or respectively together can also form "heterocyclyl";

with the further proviso that "—C(O)—N(alkyl)₂, —C(O)—N(cycloalkyl)₂, —C(O)—N(cycloalkylalkyl)₂, —C(O)—N(arylalkyl)₂, —C(O)—N(aryl)₂, —C(O)—N(heteroaryl)₂" are excluded from above substituents group (iv);

wherein optionally the other one of R2, R3 being "alkyl, cycloalkyl, cycloalkylalkyl, aryl, arylalkyl, heteroaryl" can in turn independently from each other be additonally substituted with at least one substituent, identical or different, selected from above substituents group (ii);

wherein optionally the other one of R2, R3 being "alkyl, cycloalkyl, cycloalkylalkyl, aryl, arylalkyl, heteroaryl" and being substituted with at least one substituent, identical or different, selected from above substituents group (iv) and, optionally, also (ii), can optionally be further substituted in their substituents selected from above substituents group (iv) and, optionally, also (ii), with at least one substituent, identical or different, selected from above substituents group (iii);

with the sixth proviso that, if R1, R1* are present (n is 1) and together independently form "=S or =S$^+$—O" and R2, R3 are independently selected from the group consisting of "hydrogen, alkyl, cycloalkyl, cycloalkylalkyl, aryl, arylalkyl", each of R2, R3 being "alkyl, cycloalkyl, cycloalkylalkyl, aryl, arylalkyl" must be substituted with at least one substituent selected from the group consisting of:

(v) "heterocyclyl, heterocyclylalkyl, heteroaryl, heteroarylalkyl, —CF3, —N$_3$, —NH$_2$, —NHX800, —NX801X802, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—X803, —C(O)O—X804, —C(O)NH—X805, —C(O)NX806X807, —O-aryl, —O—arylalkyl, —O-heteroaryl, —O-heteroarylalkyl, —O-heterocyclyl, —O—heterocyclylalkyl, —O(—X808-O)$_i$—H(i=1, 2, 3, 4, 5), —O(—X809-O)$_j$—X810 (j=1, 2, 3, 4, 5), —OC(O)—X811, —OC(O)—O—X812, —OC(O)—NHX813, —O—C(O)—NX814X815, —OP(O)(OX816)(OX817), —OSi(X818)(X819)(X820), —OS(O$_2$)—X821, —NHC(O)—X822, —NX823C(O)—X824, —NH—C(O)—O—X825, —NH—C(O)—NH—X826, —NH—C(O)—NX827X828, —NX829-C(O)—O—X830, —NX831-C(O)—NH—X832, —NX833-C(O)—NX834X835, —NHS(O$_2$)—X836, —NX837S(O$_2$)X838, —S—X839, —S(O)—X841, —S(O$_2$)—X841, —S(O$_2$)NH—X842, —S(O$_2$)NX843X844, —S(O$_2$)O—X845, —P(O)(OX846)(OX847), —Si(X848)(X849)(X850), —C(NH)—NH$_2$, —C(NX851)-NH$_2$, —C(NH)—NHX852, —C(NH)—NX853X854, —C(NX855)-NHX856, —C(NX857)-NX858X859, —NH—C(O)—NH—O—X860, —NH—C(O)—NX861-O—X862, —NX863-C(O)—NX864-O—X865, —N(—C(O)—NH—O—X866)$_2$, —N(—C(O)—NX867-O—X868)$_2$, —N(—C(O)—NH—O—X869)(—C(O)—NX870-O—X871), —C(S)—X872, —C(S)—O—X873, —C(S)—NH—X874, —C(S)—NX875X876, —C(O)—NH—O—X877, —C(O)—NX878-O—X879, —C(S)—NH—O—X880, —C(S)—NX881-O—X882, —C(O)—NH—NH—X883, —C(O)—NH—NX884X885, —C(O)—NX886-NX887X888, —C(S)—NH—NH—X889, —C(S)—NH—NX890X891, —C(S)—NX892-NX893X894, —C(O)—C(O)—O—X895, —C(O)—C(O)—NH$_2$, —C(O)—C(O)—NHX896, —C(O)—C(O)—NX897X898, —C(S)—C(O)—O—X899, —C(O)—C(S)—O—X900, —C(S)—C(S)—O—X901, —C(S)—C(O)—NH$_2$, —C(S)—C(O)—NHX902, —C(S)—C(O)—NX903X904, —C(S)—C(S)—NH$_2$, —C(S)—C(S)—NHX905, —C(S)—C(S)—NX906X907, —C(O)—C(S)—NH$_2$, —C(O)—C(S)—NHX908, —C(O)—C(S)—NX909X910";

wherein X800, X801, X802, X803, X804, X805, X806, X807, X808, X809, X810, X811, X812, X813, X814, X815, X816, X817, X818, X819, X820, X821, X822, X823, X824, X825, X826, X827, X828, X829, X830, X831, X832, X833, X834, X835, X836, X837, X838, X839, X840, X841, X842, X843, X844, X845, X846, X847, X848, X849, X850, X851, X852, X853, X854, X855, X856, X857, X858, X859, X860, X861, X862, X863, X864, X865, X866, X867, X868, X869, X870, X871, X872, X873, X874, X875, X876, X877, X878, X879, X880, X881, X882, X883, X884, X885, X886, X887, X888, X889, X890, X891, X892, X893, X894, X895, X896, X897, X898, X899, X900, X901, X902, X903, X904, X905, X906, X907, X908, X909, X910, X911, X912 are independently from each other selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively X806, X807 and/or X814, X815 and/or X827, X828 and/or X834, X835 and/or X843, X844 and/or X853, X854 and/or X858, X859 and/or X875, X876 and/or X884, X885 and/or X887, X888 and/or X890, X891 and/or X893, X894 and/or X897, X898 and/or X903, X904 and/or X906, X907 and/or X909, X910 and/or respectively together can also form "heterocyclyl";

wherein optionally each of R2, R3 being "alkyl, cycloalkyl, cycloalkylalkyl, aryl, arylalkyl" can in turn independently from each other be additionally substituted with at least one substituent, identical or different, selected from above substituents group (ii);

wherein optionally each of R2, R3 being "alkyl, cycloalkyl, cycloalkylalkyl, aryl, arylalkyl" and being substituted with at least one substituent, identical or different, selected from above substituents group (v) and, optionally, also (ii), can optionally be further substituted in their substituents selected from above substituents group (v) and, optionally, also (ii), with at least one substituent, identical or different, selected from above substituents group (iii);

m independently is 1 or 2;

R4$_m$, R5$_m$, R6, R7, R8, R9, R10, R11, R12, R13, R14, R15, R16, R17, R18, R19, R20, R21, R22 are independently from each other selected from the group consisting of:

(i) "hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHX1001, —NX1002X1003, —NO$_2$, —OH, =O, —OCF$_3$, —SH, —O—SO$_3$H, —OP(O)(OH)$_2$, —CHO, —COOH, —C(O)—NH$_2$, —SO$_3$H, —P(O)(OH)$_2$, —C(O)X1004, —C(O)O—X1005, —C(O)NH—X1006, —C(O)—NX1007X1008, —O—X1009, —O(—X1010-O)$_k$—H (k=1, 2, 3, 4, 5), —O(—X1011-O)$_l$—X1012 (l=1, 2, 3, 4, 5), —OC(O)—X1013, —OC(O)—O—X1014, —OC(O)—NHX1015, —O—C(O)—NX1016X1017, —OP(O)(OX1018)(OX1019), —OSi(X1020)(X1021)(X1022), —OS(O$_2$)—X1023, —NHC(O)—NH$_2$, —NHC(O)—X1024, —NX1025C(O)—X1026, —NH—C(O)—O—X1027, —NH—C(O)—NH—X1028, —NH—C(O)—NX1029X1030, —NX1031-C(O)—O—X1032, —NX1033-C(O)—NH—X1034, —NX1035-C(O)—NX1036X1037, —NHS(O$_2$)—X1038, —NX1039S(O$_2$)—X1040, —S—X1041, —S(O)—X1042, —S(O$_2$)—X1043, —S(O$_2$)—NH—X1044, —S(O$_2$)—NX1045X1046, —S(O$_2$)O—X1047, —P(O)(OX1048)(OX1049), —Si(X1050)(X1051)(X1052), —C(NH)—NH$_2$, —C(NX1053)-NH$_2$, —C(NH)—NHX1054, —C(NH)—NX1055X1056, —C(NX1057)-NHX1058, —C(NX1059)-NX1060X1061, —NH—C(O)—NH—O—X1062, —NH—C(O)—NX1063-O—X1064, —NX1065-C(O)—NX1066-O—X1067, —N(—C(O)—NH—O—X1068)$_2$, —N(—C(O)—NX1069-O—X1070)$_2$, —N(—C(O)—NH—O—X1071)(—C(O)—NX1072-O—X1073), —C(S)X1074, —C(S)—O—X1075, —C(S)—NH—X1076, —C(S)—NX1077X1078, —C(O)—NH—O—X1079, —C(O)—NX1080-O—X1081, —C(S)—NH—O—X1082, —C(S)—NX1083-O—X1084, —C(O)—NH—NH—X1085, —C(O)—NH—NX1086X1087, —C(O)—NX1088-NX1089X1090, —C(S)—NH—NH—X1091, —C(S)—NH—NX1092X1093, —C(S)—NX1094-NX1095X1096, —C(O)—C(O)—O—X1097, —C(O)—C(O)—NH$_2$, —C(O)—C(O)—NHX1098, —C(O)—C(O)—NX1099X1100, —C(S)—C(O)—O—X1101, —C(O)—C(S)—O—X1102, —C(S)—C(S)—O—X1103, —C(S)—C(O)—NH$_2$, —C(S)—C(O)—NHX1104, —C(S)—C(O)—NX1105X1106, —C(S)—C(S)—NH$_2$, —C(S)—C(S)—NHX1107, —C(S)—C(S)—NX1108X1109, —C(O)—C(S)—NH$_2$, —C(O)—C(S)—NHX1110, —C(O)—C(S)—NX1111X1112";

wherein X1001, X1002, X1003, X1004, X1005, X1006, X1007, X1008, X1009, X1010, X1011, X1012, X1013, X1014, X1015, X1016, X1017, X1018, X1019, X1020, X1021, X1022, X1023, X1024, X1025, X1026, X1027, X1028, X1029, X1030, X1031, X1032, X1033, X1034, X1035, X1036, X1037, X1038, X1039, X1040, X1041, X1042, X1043, X1044, X1045, X1046, X1047, X1048, X1049, X1051, X1051, X1052, X1053, X1054, X1055, X1056, X1057, X1058, X1059, X1060, X1061, X1062, X1063, X1064, X1065, X1066, X1067, X1068, X1069, X1070, X1071, X1072, X1073, X1074, X1075, X1076, X1077, X1078, X1079, X1080, X1081, X1082, X1083, X1084, X1085, X1086, X1087, X1088, X1089, X1090, X1091, X1092, X1093, X1094, X1095, X1096, X1097, X1098, X1099, X1100, X1101, X1102, X1103, X1104, X1105, X1106, X1107, X1108, X1109, X1110, X1111, X1112 are independently from each other selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively X1007, X1008 and/or X1016, X1017 and/or X1029, X1030 and/or X1036, X1037 and/or X1045, X1046 and/or X1055, X1056 and/or X1060, X1061 and/or X1077, X1078 and/or X1086, X1087 and/or X1089, X1090 and/or X1092, X1093 and/or X1095, X1096 and/or X1099, X1100 and/or X1105, X1106 and/or X1108, X1109 and/or X1111, X1112 and/or respectively together can also form "heterocyclyl";

wherein optionally above substituents of substituents group (i) can in turn independently from each other be substituted with at least one substituent, identical or different, selected from the group consisting of:

(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHX1201, —NX1202X1203, —NO$_2$, —OH, =O, —OCF$_3$, —SH, —O—SO$_3$H, —OP(O)(OH)$_2$, —CHO, —COOH, —C(O)—NH$_2$, —SO$_3$H, —P(O)(OH)$_2$, —C(O)—X1204, —C(O)O—X1205, —C(O)—NH—X1206, —C(O)—NX1207X1208, —O—X1209, —O(—X1210-O)$_m$—H(m=1, 2, 3, 4, 5), —O(—X1211-O)$_n$—X1212 (n=1, 2, 3, 4, 5), —OC(O)—X1213, —OC(O)—O—X1214, —OC(O)—NHX1215, —O—C(O)—NX1216X1217, —OP(O)(OX1218)(OX1219), —OSi(X1220)(X1221)(X1222), —OS(O$_2$)—X1223, —NHC(O)—NH$_2$, —NHC(O)—X1224, —NX1225C(O)—X1226, —NH—C(O)—O—X1227, —NH—C(O)—NH—X1228, —NH—C(O)—NX1229X1230, —NX1231-C(O)—O—X1232, —NX1233-C(O)—NH—X1234, —NX1235-C(O)—NX1236X1237, —NHS(O$_2$)—X1238, —NX1239S(O$_2$)—X1240, —S—X1241, —S(O)—X1242, —S(O$_2$)—X1243, —S(O$_2$)NH—X1244, —S(O$_2$)NX1245X1246, —S(O$_2$)O—X1247, —P(O)(OX1248)(OX1249), —Si(X1250)(X1251)(X1252), —C(NH)—NH$_2$, —C(NX1253)-NH$_2$, —C(NH)—NHX1254, —C(NH)—NX1255X1256, —C(NX1257)-NHX1258, —C(NX1259)-NX1260X1261, —NH—C(O)—NH—O—X1262, —NH—C(O)—NX1263-O—X1264, —NX1265-C(O)—NX1266-O—X1267, —N(—C(O)—NH—O—X1268)$_2$, —N(—C(O)—NX1269-O—X1270)$_2$, —N(—C(O)—NH—O—X1271)(—C(O)—NX1272-O—X1273), —C(S)—X1274, —C(S)—O—X1275, —C(S)—NH—X1276, —C(S)—NX1277X1278, —C(O)—NH—O—X1279, —C(O)—NX1280-O—X1281, —C(S)—NH—O—X1282, —C(S)—NX1283-O—X1284, —C(O)—NH—NH—X1285, —C(O)—NH—NX1286X1287, —C(O)—NX1288-NX1289X1290, —C(S)—NH—NH—X1291, —C(S)—NH—NX1292X1293, —C(S)—NX1294-NX1295X1296, —C(O)—C(O)—O—X1297, —C(O)—C(O)—NH$_2$, —C(O)—C(O)—NHX1298, —C(O)—C(O)—NX1299X1300, —C(S)—C(O)—O—X1301, —C(O)—C(S)—O—X1302, —C(S)—C(S)—O—X1303, —C(S)—C(O)—NH$_2$, —C(S)—C(O)—NHX1304, —C(S)—C(O)—NX1305X1306, —C(S)—C(S)NH$_2$, —C(S)—C(S)—NHX1307, —C(S)—C(S)—NX1308X1309, —C(O)—C(S)—NH$_2$, —C(O)—C(S)—NHX1310, —C(O)—C(S)—NX1311X1312";

wherein X1201, X1202, X1203, X1204, X1205, X1206, X1207, X1208, X1209, X1210, X1211, X1212, X1213, X1214, X1215, X1216, X1217, X1218, X1219, X1220, X1221, X1222, X1223, X1224, X1225, X1226, X1227, X1228, X1229, X1230, X1231, X1232, X1233, X1234, X1235, X1236, X1237, X1238, X1239, X1240, X1241, X1242, X1243, X1244, X1245, X1246, X1247, X1248, X1249, X1250, X1251, X1252, X1253, X1254, X1255, X1256, X1257, X1258, X1259, X1260, X1261, X1262, X1263, X1264, X1265, X1266, X1267, X1268, X1269, X1270, X1271, X1272, X1273, X1274, X1275, X1276, X1277, X1278, X1279, X1280, X1281, X1282, X1283, X1284, X1285, X1286, X1287, X1288, X1289, X1290, X1291, X1292, X1293, X1294, X1295, X1296, X1297, X1298, X1299, X1300, X1301, X1302, X1303, X1304, X1305, X1306, X1307, X1308, X1309, X1310, X1311, X1312 are independently from each other selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively X1207, X1208 and/or X1216, X1217 and/or X1229, X1230 and/or X1236, X1237 and/or X1245, X1246 and/or X1255, X1256 and/or X1260, X1261 and/or X1277, X1278 and/or X1286, X1287 and/or X1289, X1290 and/or X1292, X1293 and/or X1295, X1296 and/or X1299, X1300 and/or X1305, X1306 and/or X1308, X1309 and/or X1311, X1312 and/or respectively together can also form "heterocyclyl";

wherein optionally above substituents of substituents group (ii) can in turn independently from each other be substituted with at least one substituent, identical or different, selected from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —$CF_3$, —$N_3$, —$NH_2$, —NHX1401, —NX1402X1403, —$NO_2$, —OH, =O, —$OCF_3$, —SH, —O—$SO_3$H, —OP(O)(OH)$_2$, —CHO, —COOH, —C(O)$NH_2$, —$SO_3$H, —P(O)(OH)$_2$, —C(O)—X1404, —C(O)O—X1405, —C(O)NH—X1406, —C(O)—NX1407X1408, —O—X1409, —O(—X1410-O)$_o$—H(o=1, 2, 3, 4, 5), —O(—X1411-O)$_p$—X1412 (p=1, 2, 3, 4, 5), —OC(O)—X1413, —OC(O)—O—X1414, —OC(O)—NHX1415, —O—C(O)—NX1416X1417, —OP(O)(OX1418)(OX1419), —OSi(X1420)(X1421)(X1422), —OS($O_2$)—X1423, —NHC(O)—$NH_2$, —NHC(O)—X1424, —NX1425C(O)—X1426, —NH—C(O)—O—X1427, —NH—C(O)—NH—X1428, —NH—C(O)—NX1429X1430, —NX1431-C(O)—O—X1432, —NX1433-C(O)—NH—X1434, —NX1435-C(O)—NX1436X1437, —NHS($O_2$)—X1438, —NX1439S($O_2$)—X1440, —S—X1441, —S(O)—X1442, —S($O_2$)—X1443, —S($O_2$)NH—X1444, —S($O_2$)NX1445X1446, —S($O_2$)O—X1447, —P(O)(OX1448)(OX1449), —Si(X1450)(X1451)(X1452), —C(NH)—$NH_2$, —C(NX1453)-$NH_2$, —C(NH)—NHX1454, —C(NH)—NX1455X1456, —C(NX1457)-NHX1458, —C(NX1459)-NX1460X1461, —NH—C(O)—NH—O—X1462, —NH—C(O)—NX1463-O—X1464, —NX1465-C(O)—NX1466-O—X1467, —N(—C(O)—NH—O—X1468)$_2$, —N(—C(O)—NX1469-O—X1470)$_2$, —N(—C(O)—NH—O—X1471)(—C(O)—NX1472-O—X1473), —C(S)X1474, —C(S)—O—X1475, —C(S)—NH—X1476, —C(S)—NX1477X1478, —C(O)—NH—O—X1479, —C(O)—NX1480-O—X1481, —C(S)—NH—O—X1482, —C(S)—NX1483-O—X1484, —C(O)—NH—NH—X1485, —C(O)—NH—NX1486X1487, —C(O)—NX1488-NX1489X1490, —C(S)—NH—NH—X1491, —C(S)—NH—NX1492X1493, —C(S)—NX1494-NX1495X1496, —C(O)—C(O)—O—X1497, —C(O)—C(O)—$NH_2$, —C(O)—C(O)—NHX1498, —C(O)—C(O)—NX1499X1500, —C(S)—C(O)—O—X1501, —C(O)—C(S)—O—X1502, —C(S)—C(S)—O—X1503, —C(S)—C(O)—$NH_2$, —C(S)—C(O)—NHX1504, —C(S)—C(O)—NX1505X1506, —C(S)—C(S)—$NH_2$, —C(S)—C(S)—NHX1507, —C(S)—C(S)—NX1508X1509, —C(O)—C(S)—$NH_2$, —C(O)—C(S)—NHX1510, —C(O)—C(S)—NX1511 X1512";

wherein X1401, X1402, X1403, X1404, X1405, X1406, X1407, X1408, X1409, X1410, X1411, X1412, X1413, X1414, X1415, X1416, X1417, X1418, X1419, X1420, X1421, X1422, X1423, X1424, X1425, X1426, X1427, X1428, X1429, X1430, X1431, X1432, X1433, X1434, X1435, X1436, X1437, X1438, X1439, X1440, X1441, X1442, X1443, X1444, X1445, X1446, X1447, X1448, X1449, X1450, X1451, X1452, X1453, X1454, X1455, X1456, X1457, X1458, X1459, X1460, X1461, X1462, X1463, X1464, X1465, X1466, X1467, X1468, X1469, X1470, X1471, X1472, X1473, X1474, X1475, X1476, X1477, X1478, X1479, X1480, X1481, X1482, X1483, X1484, X1485, X1486, X1487, X1488, X1489, X1490, X1491, X1492, X1493, X1494, X1495, X1496, X1497, X1498, X1499, X1500, X1501, X1502, X1503, X1504, X1505, X1506, X1507, X1508, X1509, X1510, X1511, X1512 are independently from each other selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively X1407, X1408 and/or X1416, X1417 and/or X1429, X1430 and/or X1436, X1437 and/or X1445, X1446 and/or X1455, X1456 and/or X1460, X1461 and/or X1477, X1478 and/or X1486, X1487 and/or X1489, X1490 and/or X1492, X1493 and/or X1495, X1496 and/or X1499, X1500 and/or X1505, X1506 and/or X1508, X1509 and/or X1511, X1512 and/or respectively together can also form "heterocyclyl";

or (B) V, W are independently from each other selected from the group consisting of: "=O, =S, =$S^+$—$O^-$, geminally linked $H_2$";

R1*, R2 together independently form "heterocyclyl" or together independently form "heteroaryl"; where "heterocyclyl" and "heteroaryl" can optionally be substituted with at least one substituent selected from below substituents group (i);

R1, R3 are independently from each other selected from the group consisting of:

(i) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —$CF_3$, —$N_3$, —$NH_2$, —NHZ1, —NZ2Z3, —$NO_2$, —OH, =O, —$OCF_3$, —SH, —O—$SO_3$H, —OP(O)(OH)$_2$, —CHO, —COOH, —C(O)$NH_2$, —$SO_3$H, —P(O)(OH)$_2$, —C(O)—Z4, —C(O)O—Z5, —C(O)NH—Z6, —C(O)NZ7Z8, —O—Z9, —O(—Z10-O)$_a$—H(a=1, 2, 3, 4, 5), —O(—Z11-O)$_b$—Z12 (b=1, 2, 3, 4, 5), —OC(O—Z13, —OC(O)—O—Z14, —OC(O)—NHZ15, —O—C(O)—NZ16Z17, —OP(O)(OZ18)(OZ19), —OSi(Z20)(Z21)(Z22), —OS($O_2$)—Z23, —NHC(O)—$NH_2$, —NHC(O)—Z24, —NZ25C(O)—Z26, —NH—C(O)—O—Z27, —NH—C(O)—NH—Z28, —NH—C(O)—NZ29Z30, —NZ31-C(O)—O—Z32, —NZ33-C(O)—NH—Z34, —NZ35-C(O)—NZ36Z37, —NHS($O_2$)—Z38, —NZ39S($O_2$)—Z40, —S—Z41, —S(O)—Z42, —S($O_2$)—Z43, —S($O_2$)NH—Z44, —S($O_2$)NZ45Z46, —S($O_2$)O—Z47, —P(O)(OZ48)(OZ49), —Si(Z50)(Z51)(Z52), —C(NH)—$NH_2$, —C(NZ53)-$NH_2$, —C(NH)—NHZ54, —C(NH)—NZ55Z56, —C(NZ57)-NHZ58, —C(NZ59)-NZ60Z61, —NH—C(O)—NH—O—Z62, —NH—C(O)—NZ63-O—Z64, —NZ65-C(O)—NZ66-O—Z67, —N(—C(O)—NH—O—Z68)$_2$, —N(—C(O)—NZ69-O—Z70)$_2$, N(—C(O)—NH—O—Z71)(—C(O)—NZ72-O—Z73), —C(S)—Z74, —C(S)—O—Z75, —C(S)—NH—Z76, —C(S)—NZ77Z78, —C(O)—NH—O—Z79, —C(O)—NZ80-O—Z81, —C(S)—NH—O—Z82, —C(S)NZ83-O—Z84, —C(O)—NH—NH—Z85, —C(O)—NH—NZ86Z87, —C(O)—NZ88-NZ89Z90, —C(S)—NH—NH—Z91, —C(S)—NH—NZ92Z93, —C(S)NZ94-NZ95Z96, —C(O)—C(O)—O—Z97, —C(O)—C(O)—$NH_2$, —C(O)—C(O)—NHZ98, —C(O)—C(O)NZ99Z100, —C(S)—C(O)—O—Z101, —C(O)—C(S)—O—Z102, —C(S)—C(S)—O—Z103, —C(S)—C(O)—$NH_2$, —C(S)—C(O)—NHZ104, —C(S)—C(O)—NZ105Z106, —C(S)—C(S)—$NH_2$, —C(S)—C(S)—NHZ107, —C(S)—C(S)—NZ108Z109, —C(O)—C(S)—$NH_2$, —C(O)—C(S)—NHZ110, —C(O)—C(S)—NZ111Z112";

wherein Z1, Z2, Z3, Z4, Z5, Z6, Z7, Z8, Z9, Z10, Z11, Z12, Z13, Z14, Z15, Z16, Z17, Z18, Z19, Z20, Z21, Z22, Z23, Z24, Z25, Z26, Z27, Z28, Z29, Z30, Z31, Z32, Z33, Z34, Z35, Z36, Z37, Z38, Z39, Z40, Z41, Z42, Z43, Z44, Z45, Z46, Z47, Z48, Z49, Z50, Z51, Z52, Z53, Z54, Z55, Z56, Z57, Z58, Z59, Z60, Z61, Z62, Z63, Z64, Z65, Z66, Z67, Z68, Z69, Z70, Z71, Z72, Z73, Z74, Z75, Z76, Z77, Z78, Z79, Z80, Z81, Z82, Z83, Z84, Z85, Z86, Z87, Z88, Z89, Z90, Z91, Z92, Z93, Z94, Z95, Z96, Z97, Z98, Z99, Z100, Z101, Z102, Z103, Z104, Z105, Z106, Z107, Z108, Z109, Z110, Z111, Z112 are independently from each other selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively Z7, Z8 and/or Z16, Z17 and/or Z29, Z30 and/or Z36, Z37 and/or Z45, Z46 and/or Z55, Z56 and/or Z60, Z61 and/or Z77, Z78 and/or Z86, Z87 and/or Z89, Z90 and/or Z92, Z93 and/or Z95, Z96 and/or Z99, Z100 and/or Z105, Z106 and/or Z108, Z109 and/or Z111, Z112 and/or respectively together can also form "heterocyclyl";

wherein optionally above substituents of substituents group (i) can in turn independently from each other be substituted with at least one substituent, identical or different, selected from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —$CF_3$, —$N_3$, —$NH_2$, —NHZ201, —NZ202Z203, —$NO_2$, —OH, =O, —$OCF_3$, —SH, —O—$SO_3$H, —OP(O)(OH)$_2$, —CHO, —COOH, —C(O)—$NH_2$, —$SO_3$H, —P(O)(OH)$_2$, —C(O)—Z204, —C(O)O—Z205, —C(O)NH—Z206, —C(O)NZ207Z208, —O—Z209, —O(—Z210-O)$_c$—H(c=1, 2, 3, 4, 5), —O(—Z211-O)$_d$—Z212 (d=1, 2, 3, 4, 5), —OC(O)—Z213, —OC(O)O—Z214, —OC(O)—NHZ215, —O—C(O)—NZ216Z217, —OP(O)(OZ218)(OZ219), —OSi(Z220)(Z221)(Z222), —OS($O_2$)—Z223, —NHC(O)—$NH_2$, —NHC(O)—Z224, —NZ225C(O)Z226, —NH—C(O)—O—Z227, —NH—C(O)—NH—Z228, —NH—C(O)—NZ229Z230, —NZ231-C(O)—O—Z232, —NZ233-C(O)—NH—Z234, —NZ235-C(O)—NZ236Z237, —NHS($O_2$)—Z238, —NZ239S($O_2$)—Z240, —S—Z241, —S(O)—Z242, —S($O_2$)—Z243, —S($O_2$)NH—Z244, —S($O_2$)NZ245Z246, —S($O_2$)O—Z247, —P(O)(OZ248)(OZ249), —Si(Z250)(Z251)(Z252), —C(NH)—$NH_2$, —C(NZ253)-$NH_2$, —C(NH)—NHZ254, —C(NH)—NZ255Z256, —C(NZ257)-NHZ258, —C(NZ259)-NZ260Z261, —NH—C(O)—NH—O—Z262, —NH—C(O)—NZ263-O—Z264, —NZ265-C(O)—NZ266-O—Z267, —N(—C(O)—NH—O—Z268)$_2$, —N(—C(O)—NZ269-O—Z270)$_2$, —N(—C(O)—NH—O—Z271)(—C(O)—NZ272-O—Z273), —C(S)—Z274, —C(S)—O—Z275, —C(S)—NH—Z276, —C(S)—NZ277Z278, —C(O)—NH—O—Z279, —C(O)—NZ280-O—Z281, —C(S)—NH—O—Z282, —C(S)—NZ283-O—Z284, —C(O)—NH—NH—Z285, —C(O)—NH—NZ286Z287, —C(O)—NZ288-NZ289Z290, —C(S)—NH—NH—Z291, —C(S)—NH—NZ292Z293, —C(S)—NZ294-NZ295Z296, —C(O)—C(O)—O—Z297, —C(O)—C(O)—$NH_2$, —C(O)—C(O)—NHZ298, —C(O)—C(O)—NZ299Z300, —C(S)—C(O)—O—Z301, —C(O)—C(S)—O—Z302, —C(S)—C(S)O—Z303, —C(S)—C(O)—$NH_2$, —C(S)—C(O)—NHZ304, —C(S)—C(O)—NZ305Z306, —C(S)—C(S)—$NH_2$, —C(S)—C(S)—NHZ307, —C(S)—C(S)—NZ308Z309, —C(O)—C(S)—$NH_2$, —C(O)—C(S)—NHZ310, —C(O)—C(S)NZ311 Z312";

wherein Z201, Z202, Z203, Z204, Z205, Z206, Z207, Z208, Z209, Z210, Z211, Z212, Z213, Z214, Z215, Z216, Z217, Z218, Z219, Z220, Z221, Z222, Z223, Z224, Z225, Z226, Z227, Z228, Z229, Z230, Z231, Z232, Z233, Z234, Z235, Z236, Z237, Z238, Z239, Z240, Z241, Z242, Z243, Z244, Z245, Z246, Z247, Z248, Z249, Z250, Z251, Z252, Z253, Z254, Z255, Z256, Z257, Z258, Z259, Z260, Z261, Z262, Z263, Z264, Z265, Z266, Z267, Z268, Z269, Z270, Z271, Z272, Z273, Z274, Z275, Z276, Z277, Z278, Z279, Z280, Z281, Z282, Z283, Z284, Z285, Z286, Z287, Z288, Z289, Z290, Z291, Z292, Z293, Z294, Z295, Z296, Z297, Z298, Z299, Z300, Z301, Z302, Z303, Z304, Z305, Z306, Z307, Z308, Z309, Z310, Z311, Z312 are independently from each other selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively Z207, Z208 and/or Z216, Z217 and/or Z229, Z230 and/or Z236, Z237 and/or Z245, Z246 and/or Z255, Z256 and/or Z260, Z261 and/or Z277, Z278 and/or Z286, Z287 and/or Z289, Z290 and/or Z292, Z293 and/or Z295, Z296 and/or Z299, Z300 and/or Z305, Z306 and/or Z308, Z309 and/or Z311, Z312 and/or respectively together can also form "heterocyclyl";

wherein optionally above substituents of substituents group (ii) can in turn independently from each other be substituted with at least one substituent, identical or different, selected from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —$CF_3$, —$N_3$, —$NH_2$, —NHZ401, —NZ402Z403, —$NO_2$, —OH, =O, —$OCF_3$, —SH, —O—$SO_3$H, —OP(O)(OH)$_2$, —CHO, —COOH, —C(O)$NH_2$, —$SO_3$H, —P(O)(OH)$_2$, —C(O)—Z404, —C(O)O—Z405, —C(O)—NH—Z406, —C(O)NZ407Z408, —O—Z409, —O(—Z410-O)$_e$—H(e=1, 2, 3, 4, 5), —O(—Z411-O)$_f$Z412 (f=1, 2, 3, 4, 5), —OC(O)—Z413, —OC(O)—O—Z414, —OC(O)—NHZ415, —O—C(O)—NZ416Z417, —OP(O)(OZ418)(OZ419), —OSi(Z420)(Z421)(Z422), —OS($O_2$)—Z423, —NHC(O)—$NH_2$, —NHC(O)—Z424, —NZ425C(O)—Z426, —NH—C(O)—O—Z427, —NH—C(O)—NH—Z428, —NH—C(O)—NZ429Z430, —NZ431-C(O)—O—Z432, —NZ433-C(O)—NH—Z434, —NZ435-C(O)—NZ436Z437, —NHS($O_2$)—Z438, —NZ439S($O_2$)—Z440, —S—Z441, —S(O—Z442, —S($O_2$)—Z443, —S($O_2$)NH—Z444, —S($O_2$)NZ445Z446, —S($O_2$)O—Z447, —P(O)(OZ448)(OZ449), —Si(Z450)(Z451)(Z452), —C(NH)—$NH_2$, —C(NZ453)-$NH_2$, —C(NH)—NHZ454, —C(NH)—NZ455Z456, —C(NZ457)-NHZ458, —C(NZ459)-NZ460Z461, —NH—C(O)—NH—O—Z462, —NH—C(O)—NZ463-O—Z464, —NZ465-C(O)—NZ466-O—Z467, —N(—C(O)—NH—O—Z468)$_2$, —N(—C(O)—NZ469-O—Z470)$_2$, —N(—C(O)—NH—O—Z471)(—C(O)—NZ472-O—Z473), —C(S)—Z474, —C(S)—O—Z475, —C(S)—NH—Z476, —C(S)—NZ477Z478, —C(O)—NH—O—Z479, —C(O)—NZ480-O—Z481, —C(S—NH—

O—Z482, —C(S)—NZ483-O—Z484, —C(O)—NH—NH—Z485, —C(O)—NH—NZ486Z487, —C(O)—NZ488-NZ489Z490, —C(S)—NH—NH—Z491, —C(S)—NH—NZ492Z493, —C(S)—NZ494-NZ495Z496, —C(O)—C(O)—O—Z497, —C(O)—C(O)—NH$_2$, —C(O)—C(O)—NHZ498, —C(O)—C(O)—NZ499Z500, —C(S)—C(O)—O—Z501, —C(O)—C(S)—O—Z502, —C(S)—C(S)—O—Z503, —C(S)—C(O)—NH$_2$, —C(S)—C(O)—NHZ504, —C(S)—C(O)—NZ505Z506, —C(S)—C(S)—NH$_2$, —C(S)—C(S)—NHZ507, —C(S)—C(S)—NZ508Z509, —C(O)—C(S)—NH$_2$, —C(O)—C(S)—NHZ510, —C(O)—C(S)—NZ511 Z512";

wherein Z401, Z402, Z403, Z404, Z405, Z406, Z407, Z408, Z409, Z410, Z411, Z412, Z413, Z414, Z415, Z416, Z417, Z418, Z419, Z420, Z421, Z422, Z423, Z424, Z425, Z426, Z427, Z428, Z429, Z430, Z431, Z432, Z433, Z434, Z435, Z436, Z437, Z438, Z439, Z440, Z441, Z442, Z443, Z444, Z445, Z446, Z447, Z448, Z449, Z450, Z451, Z452, Z453, Z454, Z455, Z456, Z457, Z458, Z459, Z460, Z461, Z462, Z463, Z464, Z465, Z466, Z467, Z468, Z469, Z470, Z471, Z472, Z473, Z474, Z475, Z476, Z477, Z478, Z479, Z480, Z481, Z482, Z483, Z484, Z485, Z486, Z487, Z488, Z489, Z490, Z491, Z492, Z493, Z494, Z495, Z496, Z497, Z498, Z499, Z500, Z501, Z502, Z503, Z504, Z505, Z506, Z507, Z508, Z509, Z510, Z511, Z512 are independently from each other selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and wherein alternatively Z407, Z408 and/or Z416, Z417 and/or Z429, Z430 and/or Z436, Z437 and/or Z445, Z446 and/or Z455, Z456 and/or Z460, Z461 and/or Z477, Z478 and/or Z486, Z487 and/or Z489, Z490 and/or Z492, Z493 and/or Z495, Z496 and/or Z499, Z500 and/or Z505, Z506 and/or Z508, Z509 and/or Z511, Z512 and/or respectively together can also form "heterocyclyl";

alternatively, R1, R3 can also independently from each other be "no substituent";

n independently is 1;

m independently is 1 or 2;

R4$_m$, R5$_m$, R6, R7, R8, R9, R10, R11, R12, R13, R14, R15, R16, R17, R18, R19, R20, R21, R22 are independently from each other selected from the group consisting of:

(i) "hydrogen, alkyl, $(C_9-C_{30})$alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHZ1001, —NZ1002Z1003, —NO$_2$, —OH, =O, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—Z1004, —C(O)O—Z1005, —C(O)NH—Z1006, —C(O)NZ1007Z1008, —O—Z1009, —O(—Z1010-O)$_k$—H(k=1, 2, 3, 4, 5) —O(—Z1011-O)$_k$—Z1012 (l=1, 2, 3, 4, 5), —OC(O)—Z1013, —OC(O)—O—Z1014, —OC(O)—NHZ1015, —O—C(O)—NZ1016Z1017, —OP(O)(OZ1018)(OZ1019), —OSi(Z1020)(Z1021)(Z1022), —OS(O$_2$)—Z1023, —NHC(O)—NH$_2$, —NHC(O)—Z1024, —NZ1025C(O)—Z1026, —NH—C(O)—O—Z1027, —NH—C(O)—NH—Z1028, —NH—C(O)—NZ1029Z1030, —NZ1031-C(O)—O—Z1032, —NZ1033-C(O)—NH—Z1034, —NZ1035-C(O)—NZ1036Z1037, —NHS(O$_2$)—Z1038, —NZ1039S(O$_2$)—Z1040, —S—Z1041, —S(O)—Z1042, —S(O$_2$)—Z1043, —S(O$_2$)NH—Z1044, —S(O$_2$)NZ1045Z1046, —S(O$_2$)O—Z1047, —P(O)(OZ1048)(OZ1049), —Si(Z1050)(Z1051)(Z1052), —C(NH)—NH$_2$, —C(NZ1053)-NH$_2$, —C(NH)—NHZ1054, —C(NH)—NZ1055Z1056, —C(NZ1057, —NHZ1058, —C(NZ1059)-NZ1060Z1061, —NH—C(O)—NH—O—Z1062, —NH—C(O)—NZ1063-O—Z1064, —NZ1065-C(O)—NZ1066-O—Z1067, —N(—C(O)—NH—O—Z1068)$_2$, —N(—C(O)—NZ1069-O—Z1070)$_2$, —N(—C(O)—NH—O—Z1071)(—C(O)—NZ1072-O—Z1073), —C(S)—Z1074, —C(S)—O—Z1075, —C(S)—NH—Z1076, —C(S)—NZ1077Z1078, —C(O)—NH—O—Z1079, —C(O)—NZ1080-O—Z1081, —C(S)—NH—O—Z1082, —C(S)—NZ1083-O—Z1084, —C(O)—NH—NH—Z1085, —C(O)—NH—NZ1086Z1087, —C(O)—NZ1088-NZ1089Z1090, —C(S)—NH—NH—Z1091, —C(S)—NH—NZ1092Z1093, —C(S)—NZ1094-NZ1095Z1096, —C(O)—C(O)—O—Z1097, —C(O)—C(O)—NH$_2$, —C(O)—C(O)—NHZ1098, —C(O)—C(O)—NZ1099Z1100, —C(S)—C(O)—O—Z1101, —C(O)—C(S)—O—Z1102, —C(S)—C(S)—O—Z1103, —C(S)—C(O)—NH$_2$, —C(S)—C(O)—NHZ1104, —C(S)—C(O)—NZ1105Z1106, —C(S)—C(S)—NH$_2$, —C(S)—C(S)—NHZ1107, —C(S)—C(S)—NZ1108Z1109, —C(O)—C(S)—NH$_2$, —C(O)—C(S)—NHZ1110, —C(O)—C(S)—NZ1111Z1112";

wherein X1001, X1002, X1003, X1004, X1005, X1006, X1007, X1008, X1009, X1010, X1011, X1012, X1013, X1014, X1015, X1016, X1017, X1018, X1019, X1020, X1021, X1022, X1023, X1024, X1025, X1026, X1027, X1028, X1029, X1030, X1031, X1032, X1033, X1034, X1035, X1036, X1037, X1038, X1039, X1040, X1041, X1042, X1043, X1044, X1045, X1046, X1047, X1048, X1049, X1051, X1051, X1052, X1053, X1054, X1055, X1056, X1057, X1058, X1059, X1060, X1061, X1062, X1063, X1064, X1065, X1066, X1067, X1068, X1069, X1070, X1071, X1072, X1073, X1074, X1075, X1076, X1077, X1078, X1079, X1080, X1081, X1082, X1083, X1084, X1085, X1086, X1087, X1088, X1089, X1090, X1091, X1092, X1093, X1094, X1095, X1096, X1097, X1098, X1099, X1100, X1101, X1102, X1103, X1104, X1105, X1106, X1107, X1108, X1109, X1110, X1111, X1112 are independently from each other selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and wherein alternatively X1007, X1008 and/or X1016, X1017 and/or X1029, X1030 and/or X1036, X1037 and/or X1045, X1046 and/or X1055, X1056 and/or X1060, X1061 and/or X1077, X1078 and/or X1086, X1087 and/or X1089, X1090 and/or X1092, X1093 and/or X1095, X1096 and/or X1099, X1100 and/or X1105, X1106 and/or X1108, X1109 and/or X1111, X1112 and/or respectively together can also form "heterocyclyl";

wherein optionally above substituents of substituents group (i) can in turn independently from each other be substituted with at least one substituent, identical or different, selected from the group consisting of:

(ii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHZ1201, —NZ1202Z1203, —NO$_2$, —OH, =O, —OCF$_3$, —SH, —O—SO$_3$H, —OP(O)

(OH)$_2$, —CHO, —COOH, —C(O)NH$_2$, —SO$_3$H, —P(O)(OH)$_2$, —C(O)Z1204, —C(O)O—Z1205, —C(O)NH—Z1206, —C(O)NZ1207Z1208, —O—Z1209, —O(—Z1210-O)$_m$—H(m=1, 2, 3, 4, 5), —O(—Z1211-O)$_n$—Z1212 (n=1, 2, 3, 4, 5), —OC(O)—Z1213, —OC(O)—O—Z1214, —OC(O)—NHZ1215, —O—C(O)—NZ1216Z1217, —OP(O)(OZ1218)(OZ1219), —OSi(Z1220)(Z1221)(Z1222), —OS(O$_2$)—Z1223, —NHC(O)—NH$_2$, —NHC(O)—Z1224, —NZ1225C(O)—Z1226, —NH—C(O)O—Z1227, —NH—C(O)—NH—Z1228, —NH—C(O)—NZ1229Z1230, —NZ1231-C(O)—O—Z1232, —NZ1233-C(O)—NH—Z1234, —NZ1235-C(O)—NZ1236Z1237, —NHS(O$_2$)—Z1238, —NZ1239S(O$_2$)—Z1240, —S—Z1241, —S(O)Z1242, —S(O$_2$)—Z1243, —S(O$_2$)NH—Z1244, —S(O$_2$)NZ1245Z1246, —S(O$_2$)O—Z1247, —P(O)(OZ1248)(OZ1249), —Si(Z1250)(Z1251)(Z1252), —C(NH)—NH$_2$, —C(NZ1253)-NH$_2$, —C(NH)—NHZ1254, —C(NH)—NZ1255Z1256, —C(NZ1257)-NHZ1258, —C(NZ1259)-NZ1260Z1261, —NH—C(O)—NH—O—Z1262, —NH—C(O)—NZ1263-O—Z1264, —NZ1265-C(O)—NZ1266-O—Z1267, —N(—C(O)—NH—O—Z1268)$_2$, —N(—C(O)—NZ1269-O—Z1270)$_2$, —N(—C(O)—NH—O—Z1271)(—C(O)—NZ1272-O—Z1273), —C(S)Z1274, —C(S)—O—Z1275, —C(S)—NH—Z1276, —C(S)—NZ1277Z1278, —C(O)—NH—O—Z1279, —C(O)—NZ1280-O—Z1281, —C(S)—NH—O—Z1282, —C(S)—NZ1283-O—Z1284, —C(O)—NH—NH—Z1285, —C(O)—NH—NZ1286Z1287, —C(O)—NZ1288-NZ1289Z1290, —C(S)—NH—NH—Z1291, —C(S)—NH—NZ1292Z1293, —C(S)—NZ1294-NZ1295Z1296, —C(O)—C(O)—O—Z1297, —C(O)—C(O)—NH$_2$, —C(O)—C(O)—NHZ1298, —C(O)—C(O)—NZ1299Z1300, —C(S)—C(O)—O—Z1301, —C(O)—C(S)—O—Z1302, —C(S)—C(S)—O—Z1303, —C(S)—C(O)—NH$_2$, —C(S)—C(O)—NHZ1304, —C(S)—C(O)—NZ1305Z1306, —C(S)—C(S)—NH$_2$, —C(S)—C(S)—NHZ1307, —C(S)—C(S)—NZ1308Z1309, —C(O)—C(S)—NH$_2$, —C(O)—C(S)—NHZ1310, —C(O)—C(S)—NZ1311Z1312";

wherein Z1201, Z1202, Z1203, Z1204, Z1205, Z1206, Z1207, Z1208, Z1209, Z1210, Z1211, Z1212, Z1213, Z1214, Z1215, Z1216, Z1217, Z1218, Z1219, Z1220, Z1221, Z1222, Z1223, Z1224, Z1225, Z1226, Z1227, Z1228, Z1229, Z1230, Z1231, Z1232, Z1233, Z1234, Z1235, Z1236, Z1237, Z1238, Z1239, Z1240, Z1241, Z1242, Z1243, Z1244, Z1245, Z1246, Z1247, Z1248, Z1249, Z1250, Z1251, Z1252, Z1253, Z1254, Z1255, Z1256, Z1257, Z1258, Z1259, Z1260, Z1261, Z1262, Z1263, Z1264, Z1265, Z1266, Z1267, Z1268, Z1269, Z1270, Z1271, Z1272, Z1273, Z1274, Z1275, Z1276, Z1277, Z1278, Z1279, Z1280, Z1281, Z1282, Z1283, Z1284, Z1285, Z1286, Z1287, Z1288, Z1289, Z1290, Z1291, Z1292, Z1293, Z1294, Z1295, Z1296, Z1297, Z1298, Z1299, Z1300, Z1301, Z1302, Z1303, Z1304, Z1305, Z1306, Z1307, Z1308, Z1309, Z1310, Z1311, Z1312 are independently from each other selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively Z1207, Z1208 and/or Z1216, Z1217 and/or Z1229, Z1230 and/or Z1236, Z1237 and/or Z1245, Z1246 and/or Z1255, Z1256 and/or Z1260, Z1261 and/or Z1277, Z1278 and/or Z1286, Z1287 and/or Z1289, Z1290 and/or Z1292, Z1293 and/or Z1295, Z1296 and/or Z1299, Z1300 and/or Z1305, Z1306 and/or Z1308, Z1309 and/or Z1311, Z1312 and/or respectively together can also form "heterocyclyl";

wherein optionally above substituents of substituents group (ii) can in turn independently from each other be substituted with at least one substituent, identical or different, selected from the group consisting of:

(iii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHZ1401, —NZ1402Z1403, —NO$_2$, —OH, =O, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—Z1404, —C(O)O—Z1405, —C(O)NH—Z1406, —C(O)NZ1407Z1408, —O—Z1409, —O(—Z1410-O)$_o$—H(o=1, 2, 3, 4, 5), —O(—Z1411-O)$_p$—Z1412 (p=1, 2, 3, 4, 5), —OC(O)—Z1413, —OC(O)—O—Z1414, —OC(O)—NHZ1415, —O—C(O)—NZ1416Z1417, —OP(O)(OZ1418)(OZ1419), —OSi(Z1420)(Z1421)(Z1422), —OS(O$_2$)—Z1423, —NHC(O)—NH$_2$, —NHC(O)—Z1424, —NZ1425C(O)Z1426, —NH—C(O)—O—Z1427, —NH—C(O)—NH—Z1428, —NH—C(O)—NZ1429Z1430, —NZ1431-C(O—O—Z1432, —NZ1433-C(O)—NH—Z1434, -NZ1435-C(O)—NZ1436Z1437, —NHS(O$_2$)—Z1438, —NZ1439S(O$_2$)—Z1440, —S—Z1441, —S(O)—Z1442, —S(O$_2$)—Z1443, —S(O$_2$)NH—Z1444, —S(O$_2$)NZ1445Z1446, —S(O$_2$)O—Z1447, —P(O)(OZ1448)(OZ1449), —Si(Z1450)(Z1451)(Z1452), —C(NH)—NH$_2$, —C(NZ1453)-NH$_2$, —C(NH)—NHZ1454, —C(NH)—NZ1455Z1456, —C(NZ1457)-NHZ1458, —C(NZ1459)-NZ1460Z1461, —NH—C(O)—NH—O—Z1462, —NH—C(O)—NZ1463-O—Z1464, —NZ1465-C(O)—NZ1466-O—Z1467, —N(—C(O)—NH—O—Z1468)$_2$, —N(—C(O)—NZ1469-O—Z1470)$_2$, —N(—C(O)—NH—O—Z1471)(—C(O)—NZ1472-O—Z1473), —C(S)—Z1474, —C(S)—O—Z1475, —C(S)—NH—Z1476, —C(S)—NZ1477Z1478, —C(O)—NH—O—Z1479, —C(O)—NZ1480-O—Z1481, —C(S)—NH—O—Z1482, —C(S)—NZ1483-O—Z1484, —C(O)—NH—NH—Z1485, —C(O)—NH—NZ1486Z1487, —C(O)—NZ1488-NZ1489Z1490, —C(S)—NH—NH—Z1491, —C(S)—NH—NZ1492Z1493, —C(S)—NZ1494-NZ1495Z1496, —C(O)—C(O)—O—Z1497, —C(O)—C(O)—NH$_2$, —C(O)—C(O)—NHZ1498, —C(O)—C(O)—NZ1499Z1500, —C(S)—C(O)—O—Z1501, —C(O)—C(S)—O—Z1502, —C(S)—C(S)—O—Z1503, —C(S)—C(O)—NH$_2$, —C(S)—C(O)—NHZ1504, —C(S)—C(O)—NZ1505Z1506, —C(S)—C(S)—NH$_2$, —C(S)—C(S)—NHZ1507, —C(S)—C(S)—NZ1508Z1509, —C(O)—C(S)—NH$_2$, —C(O)—C(S)—NHZ1510, —C(O)—C(S)—NZ1511Z1512";

wherein Z1401, Z1402, Z1403, Z1404, Z1405, Z1406, Z1407, Z1408, Z1409, Z1410, Z1411, Z1412, Z1413, Z1414, Z1415, Z1416, Z1417, Z1418, Z1419, Z1420, Z1421, Z1422, Z1423, Z1424, Z1425, Z1426, Z1427, Z1428, Z1429, Z1430, Z1431, Z1432, Z1433, Z1434, Z1435, Z1436, Z1437, Z1438, Z1439, Z1440, Z1441, Z1442, Z1443, Z1444, Z1445, Z1446, Z1447, Z1448, Z1449, Z1450, Z1451, Z1452, Z1453, Z1454, Z1455, Z1456, Z1457, Z1458, Z1459, Z1460, Z1461, Z1462, Z1463, Z1464, Z1465, Z1466, Z1467, Z1468, Z1469, Z1470, Z1471, Z1472, Z1473, Z1474, Z1475, Z1476, Z1477, Z1478, Z1479, Z1480, Z1481, Z1482, Z1483, Z1484, Z1485, Z1486, Z1487, Z1488, Z1489, Z1490, Z1491, Z1492, Z1493, Z1494, Z1495, Z1496, Z1497, Z1498, Z1499, Z1500, Z1501, Z1502, Z1503, Z1504, Z1505, Z1506, Z1507, Z1508, Z1509, Z1510, Z1511, Z1512 are independently from each other selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and wherein alternatively Z1407, Z1408 and/or Z1416, Z1417 and/or Z1429, Z1430 and/or Z1436, Z1437 and/or Z1445, Z1446 and/or Z1455, Z1456 and/or Z1460, Z1461 and/or Z1477, Z1478 and/or Z1486, Z1487 and/or Z1489, Z1490 and/or Z1492, Z1493 and/or Z1495, Z1496 and/or Z1499, Z1500 and/or Z1505, Z1506 and/or Z1508, Z1509 and/or Z1511, Z1512 and/or respectively together can also form "heterocyclyl".

With regard to the alternative embodiment "no substituent" for R1 and R3, it is understood in the course of the present invention that R1 and/or R3 are not present and that the valences of the respective carbon and/or nitrogen atom, of which R1 and R3 are ligands and that are part of "heterocyclyl" or "heteroaryl", are fully used up by means of double and/or triple bonds.

With regard to R1, R1* and n, it is understood in the course of the present invention that if n is 0 substituents R1, R1* and the corresponding harbouring carbon atom are not present, i.e. the nitrogen atom harbouring R2, R3 is directly attached to the carbon atom harbouring $R4_m$, $R5_m$. If n is 1, then one carbon atom harbouring R1, R1* is present between the carbon atom harbouring $R4_m$, $R5_m$ and the nitrogen atom harbouring R2, R3.

With regard to $R4_m$, $R5_m$, and m, it is understood in the course of the present invention that if m is 1, one carbon atom harbouring one radical $R4_m$ and one radical $R5_m$ is present. If m is 2, then two carbon atoms each harbouring one radical $R4_m$ and one radical $R5_m$ are present, where all four radicals $R4_{m1}$, $R5_{m1}$, $R4_{m2}$, $R5_{m2}$ can independently from each other be identical or different.

In a further preferred embodiment, a medicament comprising at least one LHRH antagonist, in particular at least one peptidomimetic LHRH antagonist, is provided that can be used in the treatment or prophylaxis of herewithin disclosed physiological and/or pathological conditions, wherein the LHRH antagonist is selected from the group consisting of:
Compound 36 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(morpholin-4-ylmethyl)-carbamoyl]-butyl}-amide

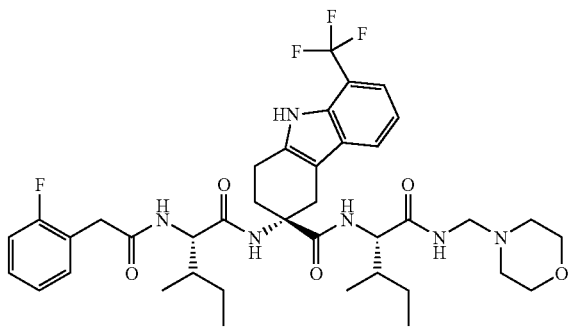

Compound 37 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(morpholin-4-ylmethyl)-thiocarbamoyl]-butyl}-amide

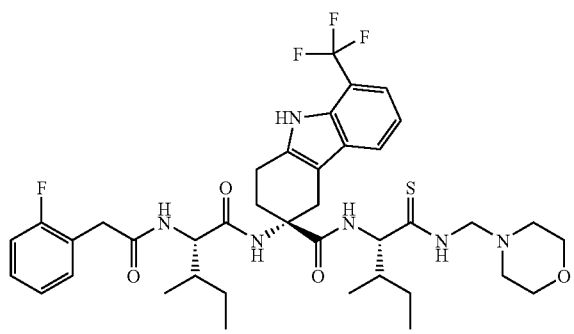

Compound 52 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(tetrahydro-pyran-4-ylmethyl)-thiocarbamoyl]-butyl}-amide

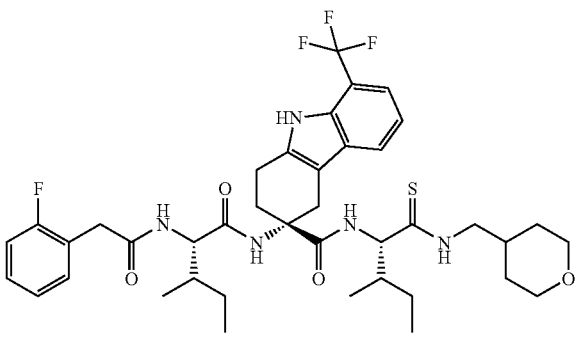

Compound 144 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(N'-phenyl-hydrazinocarbonyl)-butyl]-amide

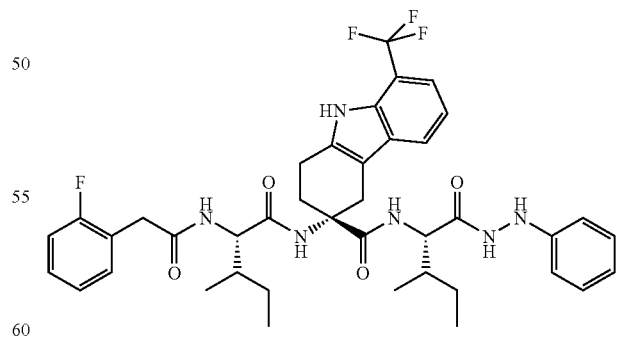

In a further preferred embodiment, a medicament comprising at least one LHRH antagonist, in particular at least one peptidomimetic LHRH antagonist, is provided that can be used in the treatment or prophylaxis of herewithin disclosed physiological and/or pathological conditions, wherein the LHRH antagonist is selected from the group consisting of:

(A)
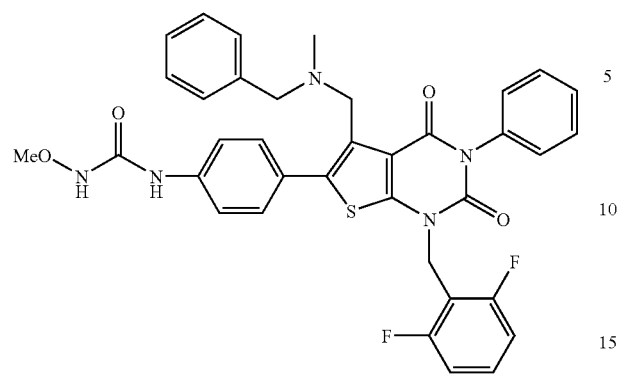
(B)
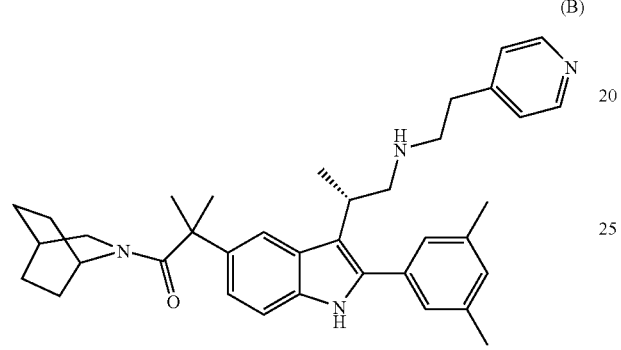
(C)
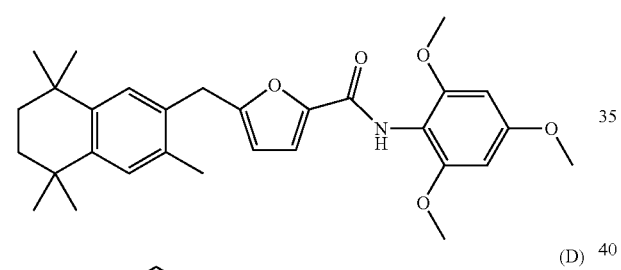
(D)
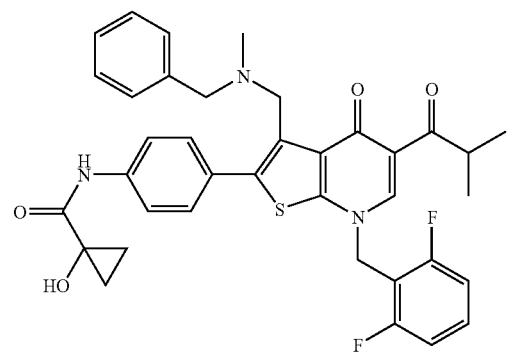
(E)
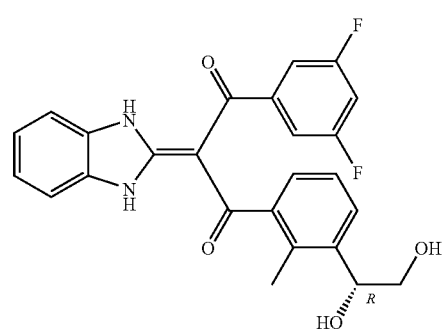
-continued
(F)
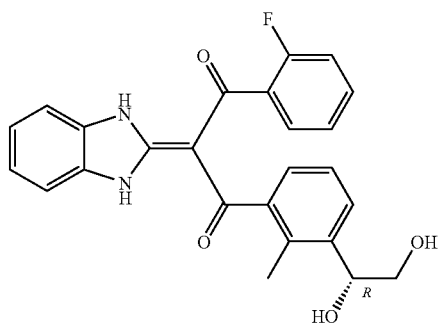
(G)
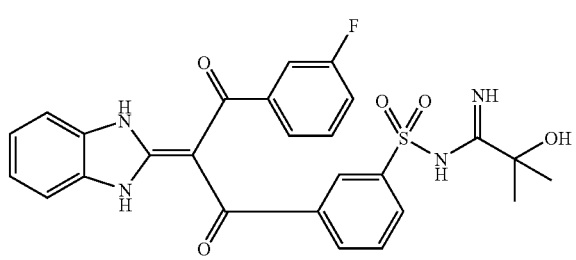
(H)
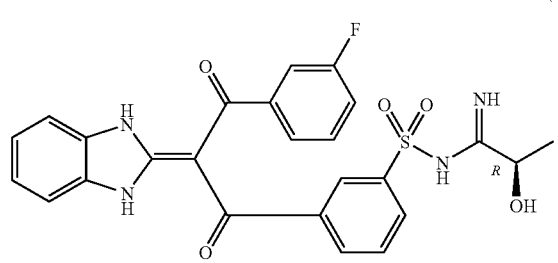
(I)
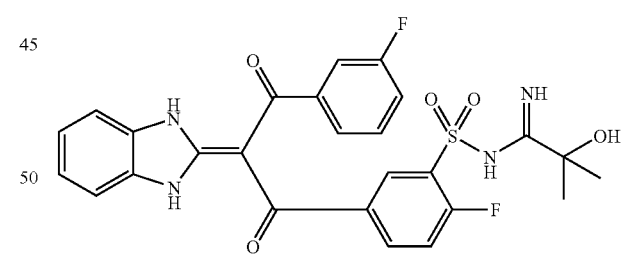
(J)
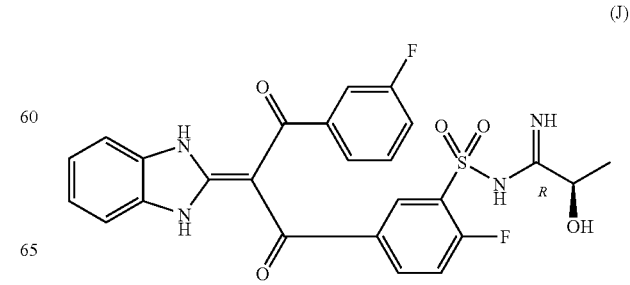

(K)

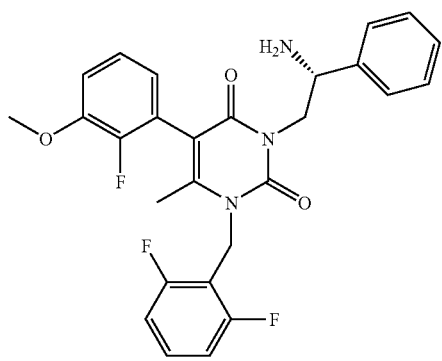

(L)

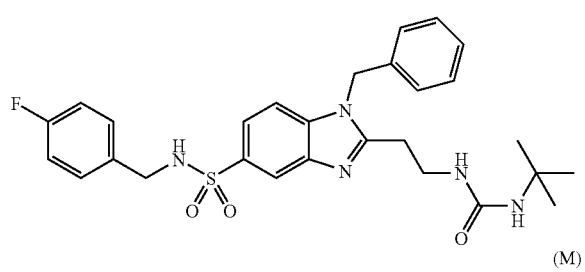

(M)

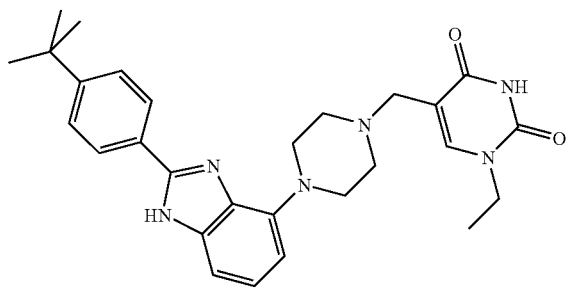

(N)

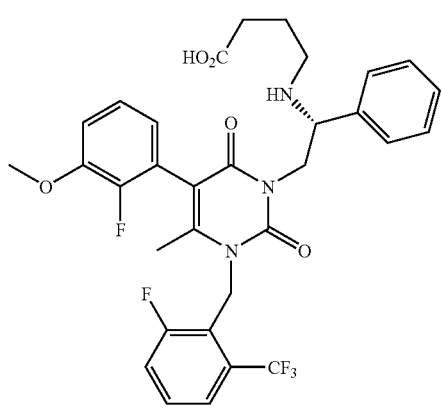

For the avoidance of doubt, if chemical name and chemical structure of the above illustrated compounds do not correspond by mistake, the chemical structure is regarded to unambiguously define the compound.

The terms indicated for explanation of the above compounds of the invention always, unless indicated otherwise in the description or in the claims, have the following meanings:

The term "unsubstituted" means that the corresponding radical, group or moiety has no substituents.

The term "substituted" means that the corresponding radical, group or moiety has one or more substituents. Where a radical has a plurality of substituents, and a selection of various substituents is specified, the substituents are selected independently of one another and do not need to be identical.

The term "alkyl" for the purposes of this invention refers to acyclic saturated or unsaturated hydrocarbon radicals which may be branched or straight-chain and have 1 to 8 carbon atoms, i.e. $C_{1-8}$-alkanyls, $C_{2-8}$-alkenyls and $C_{2-8}$-alkynyls. Alkenyls have at least one C—C double bond and alkynyls at least one C—C triple bond. Alkynyls may additionally also have at least one C—C double bond. Examples of suitable alkyl radicals are methyl, ethyl, n-propyl, isopropyl, n-butyl, isobutyl, sec-butyl, tert-butyl, n-pentyl, iso-pentyl, neo-pentyl, tert-pentyl, 2- or 3-methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl, ethylenyl (vinyl), propenyl (—CH$_2$CH═CH$_2$; —CH═CH—CH$_3$, —C(═CH$_2$)—CH$_3$), butenyl, pentenyl, hexenyl, heptenyl, octenyl, octadienyl, octade-cenyl, octadec-9-enyl, icosenyl, icos-11-enyl, (Z)-icos-11-enyl, docosnyl, docos-13-enyl, (Z)-docos-13-enyl, ethynyl, propynyl (—CH$_2$—C≡CH, —C≡C—CH$_3$), butynyl, pentynyl, hexynyl, heptynyl, octynyl, The term "$(C_9-C_{30})$alkyl" for the purposes of this invention refers to acyclic saturated or unsaturated hydrocarbon radicals which may be branched or straight-chain and have 9 to 30 carbon atoms, i.e. $C_{9-30}$-alkanyls, $C_{9-30}$-alkenyls and $C_{9-30}$-alkynyls. $C_{9-30}$-Alkenyls have at least one C—C double bond and $C_{9-30}$-alkynyls at least one C—C triple bond. $C_{9-30}$-Alkynyls may additionally also have at least one C—C double bond. Examples of suitable $(C_9-C_{30})$alkyl radicals are tetradecyl, hexadecyl, octadecyl, eicosanyl, cis-13-docosenyl (erucyl), trans-13-docosenyl(brassidyl), cis-15-tetracosenyl (nervonyl) and trans-15-tetracosenyl.

The term "cycloalkyl" for the purposes of this invention refers to saturated and partially unsaturated non-aromatic cyclic hydrocarbon groups/radicals, having 1 to 3 rings, that contain 3 to 20, preferably 3 to 12, most preferably 3 to 8 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula (I) or (II) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

The term "heterocyclyl" for the purposes of this invention refers to a mono- or polycyclic system of 3 to 20, preferably 5 or 6 to 14 ring atoms comprising carbon atoms and 1, 2, 3, 4, or 5 heteroatoms, in particular nitrogen, oxygen and/or sulfur which are identical or different. The cyclic system may be saturated, mono- or polyunsaturated but may not be aromatic. In the case of a cyclic system consisting of at least two rings the rings may be fused or spiro- or otherwise connected. Such "heterocyclyl" radicals can be linked via any ring member. The term "heterocyclyl" also includes systems in which the heterocycle is part of a bi- or polycyclic saturated, partially unsaturated and/or aromatic system, such as where the heterocycle is fused to an "aryl", "cycloalkyl", "heteroaryl" or "heterocyclyl" group as defined herein via any desired and possible ring member of the heterocycyl radical. The bonding to the compounds of the general formula (I) or (II) can be effected via any possible ring member of the heterocycyl radical. Examples of suitable "heterocyclyl" radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl.

The term "aryl" for the purposes of this invention refers to aromatic hydrocarbon systems having 3 to 14, preferably 5 to 14, more preferably 6 to 14 carbon atoms. The term "aryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the aryl radical. The bonding to the compounds of the general formula (I) or (II) can be effected via any possible ring member of the aryl radical. Examples of suitable "aryl" radicals are phenyl, biphenyl, naphthyl and anthracenyl, but likewise indanyl, indenyl, or 1,2,3,4-tetrahydronaphthyl.

The term "heteroaryl" for the purposes of this invention refers to a 3 to 14, preferably 5 to 14, more preferably 5-, 6- or 7-membered cyclic aromatic hydrocarbon radical which comprises at least 1, where appropriate also 2, 3, 4 or 5 heteroatoms, preferably nitrogen, oxygen and/or sulfur, where the heteroatoms are identical or different. The number of nitrogen atoms is preferably 0, 1, 2, or 3, and that of the oxygen and sulfur atoms is independently 0 or 1. The term "heteroaryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the heteroaryl radical. The bonding to the compounds of the general formula (I) or (II) can be effected via any possible ring member of the heteroaryl radical. Examples of suitable "heteroaryl" are pyrrolyl, thienyl, furyl, imidazolyl, thiazolyl, isothiazolyl, oxazolyl, oxadiazolyl, isoxazolyl, pyrazolyl, pyridinyl, pyrimidinyl, pyridazinyl, pyrazinyl, indolyl, quinolinyl, isoquinolinyl, imidazolyl, triazolyl, triazinyl, tetrazolyl, phthalazinyl, indazolyl, indolizinyl, quinoxalinyl, quinazolinyl, pteridinyl, carbazolyl, phenazinyl, phenoxazinyl, phenothiazinyl, acridinyl.

For the purposes of the present invention, the terms "alkylcycloalkyl", "cycloalkylalkyl", "alkyl-heterocyclyl", "heterocyclylalkyl", "alkyl-aryl", "arylalkyl", "alkyl-heteroaryl" and "heteroarylalkyl" mean that alkyl, cycloalkyl, heterocycl, aryl and heteroaryl are each as defined above, and the cycloalkyl, heterocyclyl, aryl and heteroaryl radical is bonded to the compounds of the general formula (I) or (II) via an alkyl radical, preferably $C_1$-$C_8$-alkyl radical, more preferably $C_1$-$C_4$-alkyl radical.

The term "halogen", "halogen atom" or "halogen substituent" (Hal-) for the purposes of this invention refers to one, where appropriate, a plurality of fluorine (F, fluoro), bromine (Br, bromo), chlorine (Cl, chloro), or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine, chlorine or bromine atom.

The term "intermediate dose" in the course of the present invention is defined by its higher and lower limit and has the following meaning: The higher limit of "intermediate dose" is the dose that just does not cause chemical (hormonal) castration as defined herein, wherein the lower limit of "intermediate dose" is the dose that just causes a lowering, even if a very small one, of LH, FSH and/or testosterone with regard to normal sex hormone blood levels. It lies within the knowledge of the skilled artisan to elaborate the lower and upper limit of an "intermediate dose" for each LHRH antagonist to be used on the basis of his expert knowledge and the disclosure of the present invention.

The term "peptidomimetic" in connection with LHRH antagonist in the course of the present invention refers to a peptide-derived structure, i.e. a structure that comprises one ore more amino acid residues or is derived from such amino acid residues.

In yet a further preferred embodiment, a medicament comprising at least one LHRH antagonist, in particular at least one peptidomimetic LHRH antagonist, is provided that can be used in the treatment or prophylaxis of herewithin disclosed physiological and/or pathological conditions, wherein the intermediate dose is a total monthly dose in the range of 10 mg to 150 mg LHRH antagonist, preferably a total monthly dose in the range of 10 mg to 120 mg LHRH antagonist, more preferably a total monthly dose in the range of 10 mg to 40 mg LHRH antagonists, more preferably a total monthly dose in the range of 40 mg to 150 mg LHRH antagonists, more preferably a total monthly dose in the range of 60 mg to 150 mg LHRH antagonists, more preferably a total monthly dose in the range of 60 mg to 120 mg LHRH antagonists and most preferably a total monthly dose of 10 mg, 20 mg, 30 mg, 40 mg, 60 mg, 90 mg, 120 mg, 130 mg or 150 mg LHRH antagonist.

In yet a further preferred embodiment, such total monthly dose is to be administered as one single monthly administration or is to be administered twice a month (preferably biweekly), three-times a month or four-times a month (preferably weekly).

If a total monthly dose is to be administered biweekly or weekly, for instance, the total monthly dose is the sum of each single administration, where the single administrations need not to be identical. That is a total monthly dose of 40 mg LHRH antagonist can, for instance, be administered in two biweekly administrations of 20 mg+20 mg or 30 mg+10 mg or in four weekly administrations of 10 mg+10 mg+10 mg+10 mg or 20 mg+5 mg+10 mg+5 mg. A total monthly dose of 90 mg LHRH antagonist can, for instance, be administered in two biweekly administrations of 60 mg+30 mg or 30 mg+60 mg or 45 mg+45 mg or three-times a month as 30 mg+30 mg+30 mg.

In a further preferred embodiment, a medicament comprising at least one LHRH antagonist, in particular at least one peptidomimetic LHRH antagonist, is provided that can be used in the treatment or prophylaxis of herewithin disclosed physiological and/or pathological conditions, wherein the intermediate dose is a single or multiple daily dose of 0.1 mg to 250 mg LHRH antagonist, a single or multiple daily dose of 1 mg to 60 mg LHRH antagonist, a single or multiple daily dose of 50 mg to 150 mg LHRH antagonist or a single or multiple daily dose of 50 mg, 75 mg or 150 mg LHRH antagonist, wherein the single or multiple daily dose is administered over one day, two days, three days, four days, five days, six days or more days, 1 week, 2 weeks, 3 weeks, 4 weeks, 5 weeks, 6 weeks or more weeks, 1 months, 2 months, 3 months, 4 months, 5 months, 6 months or more months, wherein the administration of each single dose can be followed by a treatment-free period of one day, two days, three days, four days, five days, six days or more days, 1 week, 2 weeks, 3 weeks, 4 weeks, 5 weeks, 6 weeks or more weeks, 1 months, 2 months, 3 months, 4 months, 5 months, 6 months or more months.

In a preferred embodiment, a medicament comprising at least one LHRH antagonist, in particular at least one peptidomimetic LHRH antagonist, is provided that can be used in the treatment or prophylaxis of herewithin disclosed physiological and/or pathological conditions with the herein disclosed doses, wherein the at least one LHRH antagonist is to be administered over a treatment period of 1 or 2 months followed by a treatment-free period of 1, 2, 3, 4 or 5 months, preferably 2 months or 5 months (one treatment cycle).

The term "treatment cycle" in the course of the present invention is defined as a treatment period of 1 or 2 months followed by a treatment-free period of at least one and up to five months. That is the shortest treatment cycle consists of a one-month treatment period and a one-month treatment-free period, whereas the longest treatment cycle consists of a two-months treatment period and a five-months treatment-free period. Preferred are a treatment cycle with a one-month or two-months treatment period and a two-months treatment-free period and a treatment cycle with a one-month or two-months treatment period and a five-months treatment-free period.

In a further preferred embodiment, a medicament comprising at least one LHRH antagonist, in particular at least one peptidomimetic LHRH antagonist, is provided that can be used in the treatment or prophylaxis of herewithin disclosed physiological and/or pathological conditions with the herein disclosed doses, wherein the at least one LHRH antagonist is to be administered in a dose of:

5 mg LHRH antagonist four-times a month (preferably weekly) or three-times a month or twice a month (preferably biweekly), or
  10 mg LHRH antagonist four-times a month (preferably weekly) or three-times a month or twice a month (preferably biweekly), or
  15 mg LHRH antagonist four-times a month (preferably weekly) or three-times a month or twice a month (preferably biweekly), or
  30 mg LHRH antagonist four-times a month (preferably weekly) or three-times a month or twice a month (preferably biweekly), or
  60 mg LHRH antagonist as one single administration followed by 30 mg LHRH antagonist as one single administration two weeks later, or
  60 mg LHRH antagonist twice a month (preferably biweekly),
over a treatment period of 1 or 2 months followed by a treatment-free period of 1, 2, 3, 4 or 5 months, preferably 2 months or 5 months (one treatment cycle).

In yet a further preferred embodiment, a medicament comprising at least one LHRH antagonist, in particular at least one peptidomimetic LHRH antagonist, is provided that can be used in the treatment or prophylaxis of herewithin disclosed physiological and/or pathological conditions with the herein disclosed doses, wherein the treatment cycle is repeated after the end of the treatment-free period of the preceding treatment cycle once, twice, three-times, four-times, five-times or continuously (chronic treatment) and wherein each respective succeeding treatment cycle can be identical or different to each respective preceding treatment cycle.

That is, for instance, a treatment cycle with a one-month or two-months treatment period and a two-months treatment-free period can be followed by a treatment cycle with a one-month or two-months treatment period and a five-months treatment-free period or vice versa. A chronic treatment could, for instance, consist of consecutive treatment cycles with a one-month or two-months treatment period and a two-months treatment-free period or of consecutive treatment cycles with a one-month of two-months treatment period and a five-months treatment-free period or of consecutive treatment cycles with alternating one-month or two-months treatment periods and two- or five-months treatment-free periods in all possible ways.

It is known in the prior art, that testosterone castration levels of castrates and boys before reaching puberty are in the range between 0.3 to 1.2 ng/mL ("Labor und Diagnose, Herausgegeben von Lothar Thomas, 5. Erweiterte Auflage 2000, page 44, 44.2.5 Referenzbereich").

In the course of the present invention, the terms "hormone" and "hormonal" within for instance the terms "hormone castration", "chemical (hormonal) castration" or "hormone withdrawal symptoms" refer to follicle stimulating hormone (FSH), luteinizing hormone (LH) and/or testosterone. Preferably, chemical (hormonal) castration is a testosterone castration and refers to a testosterone blood level of equal or below 1.2 ng/mL, preferably 0.5 ng/mL.

In a further preferred embodiment, a medicament comprising at least one LHRH antagonist, in particular at least one peptidomimetic LHRH antagonist, is provided that can be used in the treatment or prophylaxis of herewithin disclosed physiological and/or pathological conditions with the herein disclosed doses, wherein the chemical (hormonal) castration is a testosterone castration referring to a testosterone blood level of equal or below 1.2 ng/mL, preferably 0.5 ng/mL.

The at least one LHRH antagonist as defined herein can be administered to various mammalian species, including human, for the herewith disclosed treatments of such mammals.

For the purpose of the present invention, all mammalian species are regarded as being comprised. Preferably, such mammals are selected from the group consisting of "human, domestic animals, cattle, livestock, pets, cow, sheep, pig, goat, horse, pony, donkey, hinny, mule, hare, rabbit, cat, dog, guinea pig, hamster, rat, mouse". More preferably, such mammals are human, including male human and female human.

The treatments of the present invention are surprisingly characterized in that the people treated do not show hormone withdrawal symptoms. It was surprisingly found that the applied doses of LHRH antagonists—in the course of the favorable dosage/administration schemes—are sufficiently low to prevent chemical (hormonal) castration, in particular testosterone castration, i.e. without effecting the undesired castration side effects (hormone withdrawal symptoms), while still achieving the desired therapeutic effects in the treatment of, for instance, endometriosis, BPH and/or prostate cancer.

LHRH antagonists can be prepared for use according to the present invention as illustrated in the relevant prior art. In this connection, LHRH antagonists can be present in fast-release or slow-release (depot) formulations. Slow-release (depot) formulations are preferred in order to ensure a patient-friendly treatment scheme.

Various forms of prodrugs are well known in the art and are described for instance in:

(i) Wermuth C G et al., Chapter 31: 671-696, The Practice of Medicinal Chemistry, Academic Press 1996;
  (ii) Bundgaard H, Design of Prodrugs, Elsevier 1985; and
  (iii) Bundgaard H, Chapter 5: 131-191, A Textbook of Drug Design and Development, Harwood Academic Publishers 1991.

Said references are incorporated herein by reference.

It is further known that chemical substances are converted in the body into metabolites which may where appropriate likewise elicit the desired biological effect—in some circumstances even in more pronounced form.

Any biologically active compound that was converted in vivo by metabolism from any of the at least one additional pharmacologically active substance is a metabolite within the scope and spirit of the invention.

Oral administration can take place for example in solid form as tablet, capsule, gel capsule, coated tablet, granulation or powder, but also in the form of a drinkable solution. The at least one additional pharmacologically active substance can for oral administration be combined with known and ordinarily used, physiologically tolerated excipients and carriers such as, for example, gum arabic, talc, starch, sugars such as, for example, mannitol, methylcellulose, lactose, gelatin, surface-active agents, magnesium stearate, cyclodextrins, aqueous or nonaqueous carriers, diluents, dispersants, emulsifiers, lubricants, preservatives and flavorings (e.g. essential oils). The at least one additional pharmacologically active substance can also be dispersed in a microparticulate, e.g. nanoparticulate, composition.

Non-oral administration can take place for example by intravenous, subcutaneous, intramuscular injection of sterile aqueous or oily solutions, suspensions or emulsions, by means of implants or by ointments, creams or suppositories. Administration as sustained release form is also possible where appropriate. Implants may comprise inert materials, e.g. biodegradable polymers or synthetic silicones such as, for example, silicone rubber. Intravaginal administration is possible for example by means of vaginal rings. Intrauterine administration is possible for example by means of diaphragms or other suitable intrauterine devices. Transdermal administration is additionally provided, in particular by means of a formulation suitable for this purpose and/or suitable means such as, for example, patches.

The dosage may vary within a wide range depending on type and/or severity of the physiological and/or pathophysiological condition, the mode of administration, the age, gender, bodyweight and sensitivity of the subject to be treated. It is within the ability of a skilled worker to determine a "pharmacologically effective amount" of an LHRH antagonist of the invention. Administration can take place in a single dose or a plurality of separate dosages.

Chemical Synthesis:

General Methods For Synthesizing the Compounds of Formula (II)

The compounds of formula (II) can be prepared for example in the following way:

Firstly, the compounds can be synthesized by preparing the depicted central tetra-hydrocarbazole structure

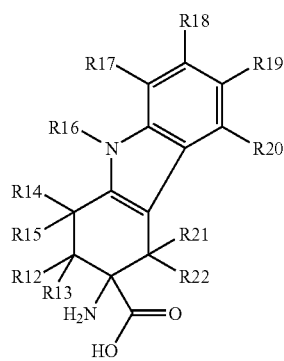

where this optionally protected tetrahydrocarbazole structure already contains the required substituents where appropriate as precursors or in protected form.

The central tetrahydrocarbazole structure is obtainable, for example, by a Fischer indole synthesis, known per se. For this purpose, a suitably substituted cyclohexanone derivative which is provided where appropriate with protective groups is condensed with the particular desired phenylhydrazine derivative which is likewise suitably substituted and, where appropriate, provided with protective groups (e.g. as described by Britten & Lockwood, *J Chem. Soc. Perkin Trans. I* 1974, 1824 or Maki et al., *Chem. Pharm. Bull.* 1973, 21, 240). The cyclohexane structure is substituted in the 4,4' position by the radicals —COOH and —$NH_2$ or where appropriate by the (protected) precursors thereof. The phenylhydrazine structure is substituted where appropriate by the radicals R17 to R20. Phenylhydrazine derivatives which are not commercially available can be prepared by processes known to the skilled worker. Positional isomers resulting where appropriate in the condensation of the cyclohexanone derivative and the phenylhydrazine derivative can be separated by chromatographic methods such as, for example, HPLC.

The derivatization of the terahydocarbazole unit can in principle be achieved in various ways known to the skilled worker, and as indicated for example in WO 03/051837 or in WO 2006/005484.

The embodiments of the invention or intermediates thereof were synthesized either by conventional liquid phase synthesis in solution (see below) or else wholly or partly on a solid phase as described in WO 2006/005484.

The synthesis of relevant building blocks like tert-butyl ((S)-1-carbamoyl-2-methylbutyl)carbamate (Boc-Ile-$NH_2$), tert-butyl ((S)-2-methyl-1-thiocarbamoylbutyl)-carbamate (Boc-Ile thioamide), (S)-2-amino-3-methylpentanamide (H-Ile thioamide), (R/S)-3-((S)-2-benzyloxycarbonylamino-3-methyl-pentanoylamino)-6,8-dichloro-2,3,4,9-tetrahydro-1H-carbazole-3-carboxylic acid (Z—(S)-Ile-(R/S)-(6,8-Cl)-Thc-OH) and the synthesis of C-terminal substituted amides in solution as exemplified by the synthesis of (S)-2-{[(R/S)-3-((S)-2-benzyloxycarbonylamino-3-methylpentanoyl-amino)-6,8-dichloro-2,3,4,9-tetrahydro-1H-carbazole-3-carbonyl]amino}-3-methylpentanoic acid ((S)—Z-Ile-(R/S)-(6,8-Cl)-Thc-(S)-Ile-OH)+R1-NH—R2 has been described in WO 2006/005484.

Purification of the Crude Reaction Products (I.E. Mixtures of Diastereoisomers) by Semipreparative HPLC Analytical and semipreparative HPLC systems from Shimadzu; column 250-50, LiChrospher® 100, RP18 (12 μm) from Merck; flow rate 60 ml/min.

Eluents: A=970 ml of water+30 ml of ACN+1 ml of TFA
B=300 ml of water+700 ml of ACN+1 ml of TFA
UV detector 220 nm.

All products were isolated by gradient elution.

The crude products are dissolved in eluent B (DMF added for products of low solubility) and purified in portions on the column (e.g. dissolve 500 mg of crude product in 15 ml of B and separate in one portion). The separation conditions in this case depend on the peptide sequence and nature and amount of the impurities and are established experimentally beforehand on the analytical column.

A typical gradient is: 60% B-100% B in 30 minutes.

If the crude products are mixtures of diastereomers, they are separated by this method.

The isolated fractions are checked by analytical HPLC. ACN and TFA are removed in a rotary evaporator, and the remaining aqueous concentrate is lyophilized.

The compounds of the present invention were prepared as indicated below. The analytical characterization of the compounds of the invention took place by $^1$H-NMR spectroscopy and/or mass spectrometry.

The chemicals and solvents employed were obtained commercially from usual suppliers (Acros, Avocado, Aldrich, Bachem, Fluka, Lancaster, Maybridge, Merck, Sigma, TCI etc.) or synthesized by processes known to the skilled worker.

For the exemplary embodiments indicated below, chiral building blocks were usually employed in enantiopure form. In the case of the tetrahydrocarbazole precursor, the racemic building block was employed. Final products were purified by semipreparative HPLC and characterized in the form of the pure diastereomers.

| List of abbreviations used: | |
|---|---|
| e.g. | for example |
| DBU | 1,8-diazabicyclo[5.4.0]undec-7-ene |
| HOBt | 1-hydroxybenzotriazole |
| Fmoc | 9-fluoroenylmethoxycarbonyl |
| Boc | tert-butyloxycarbonyl |
| Z | benzyloxycarbonyl |
| Z-Cl | benzyloxycarbonyl chloride |
| Boc$_2$O | di-tert-butyl dicarbonate |
| Bzl | benzyl |
| AA | amino acid |
| EDT | 1,2-ethanedithiol |
| DEAD | diethyl azodicarboxylate |
| DIC | N,N'-diisopropylcarbodiimide |
| DCC | N,N'-dicyclohexylcarbodiimide |
| HATU | N,N,N',N'-tetramethyl-O-(7-azabenzotriazol-1-yl)uronium hexafluorophosphate |
| HOAt | 1-hydroxy-7-azabenzotriazole |
| PyBop | (benzotriazol-1-yloxy)tripyrrolidinophosphonium hexafluorophosphate |
| OSu | N-hydroxysuccinimidyl |
| DIPEA | diisopropylethylamine |
| DMAP | N,N'-dimethylaminopyridine |
| DBU | 1,8-diazabicyclo[5.4.0]undec-7-ene |
| NMM | N-methylmorpholine |
| TFA | trifluoroacetic acid |
| DCM | dichloromethane |
| DMF | N,N'-dimethylformamide |
| DMA | N,N'-dimetylacetamide |
| ACN | acetonitrile |
| THF | tetrahydrofuran |
| Me | methyl |
| MeOH | methanol |
| Lawesson's reagent | 2,4-bis(4-methoxyphenyl)-1,3-dithia-2,4-diphosphetane 2,4-disulfide |
| Thc | 3-amino-2,3,4,9-tetrahydro-1H-carbazole-3-carboxylic acid |
| Ala | alanine(yl) |
| Val | valine(yl) |
| Ile | isoleucine(yl) |
| Leu | leucine(yl) |
| Gln | glutamine(yl) |
| Asn | asparagine(yl) |
| Tyr | tyrosine(yl) |
| hTyr | homo-tyrosine(yl) |
| Arg | arginine(yl) |
| Lys | lysine(yl) |
| RT | room temperature |
| m.p. | melting point |
| ml | milliliter |
| min | minute |
| h | hour |
| ELISA | enzyme linked immunosorbent assay |
| HEPES | N-(2-hydroxyethyl)piperazine-N'-2-ethanesulfonic acid |
| DMEM | Dulbecco's modified Eagles medium |
| RIA | radio immuno assay |
| LHRH | luteinizing hormone releasing hormone |
| LH | luteinizing hormone |
| NK1 | neurokinin 1 |
| NK2 | neurokinin 2 |
| PG | protecting group |

The compounds of the invention were named using the AutoNom 2000 software (ISIS™/Draw 2.5; MDL).

The contents of all cited references are hereby incorporated by reference in their entirety. The invention is explained in more detail by means of the following examples without, however, being restricted thereto.

EXAMPLES

Example 1

Study subjects are treated with compound (76) with the following doses according to the following administration schemes:
in a 3 month trial, 75 mg or 150 mg compound (76) administered perorally daily as a single dose on day 2-7 of the menstrual cycle
in a 3 months trial, 75 mg, 100 mg or 150 mg compound (76) administered perorally daily as a single dose on day 2-7 of the menstrual cycle followed by a 3 months treatment-free period
in a 6 months trial, 75 mg or 150 mg compound (76) administered perorally daily as a single dose
50 mg or 150 mg per compound (76) administered daily as a single dose over 42 days (6 weeks)

The treatments with compound (76) according to above doses and administration schemes demonstrate the effectiveness of the treatments of the invention, in particular in endometriosis, benign prostate hyperplasia (BPH) and prostate cancer.

The results further demonstrate that chemical (hormonal) castration can be successfully prevented.

Example 2

Study subjects are treated with compound (68) with the following doses according to the following administration schemes:
in a 3 month trial, 75 mg or 150 mg compound (68) administered perorally daily as a single dose on day 2-7 of the menstrual cycle
in a 3 months trial, 75 mg, 100 mg or 150 mg compound (68) administered perorally daily as a single dose on day 2-7 of the menstrual cycle followed by a 3 months treatment-free period
in a 6 months trial, 75 mg or 150 mg compound (68) administered perorally daily as a single dose
50 mg or 150 mg per compound (68) administered daily as a single dose over 42 days (6 weeks)

The treatments with compound (68) according to above doses and administration schemes demonstrate the effectiveness of the treatments of the invention, in particular in endometriosis, benign prostate hyperplasia (BPH) and prostate cancer.

The results further demonstrate that chemical (hormonal) castration can be successfully prevented.

Example 3

Study subjects are treated with compound 36 with the following doses according to the following administration schemes:
in a 3 month trial, 75 mg or 150 mg compound 36 administered perorally daily as a single dose on day 2-7 of the menstrual cycle
in a 3 months trial, 75 mg, 100 mg or 150 mg compound 36 administered perorally daily as a single dose on day 2-7 of the menstrual cycle followed by a 3 months treatment-free period
in a 6 months trial, 75 mg or 150 mg compound 36 administered perorally daily as a single dose
50 mg or 150 mg per compound 36 administered daily as a single dose over 42 days (6 weeks)

The treatments with compound 36 according to above doses and administration schemes demonstrate the effectiveness of the treatments of the invention, in particular in endometriosis, benign prostate hyperplasia (BPH) and prostate cancer.

The results further demonstrate that chemical (hormonal) castration can be successfully prevented.

Example 4

Study subjects are treated with compound 37 with the following doses according to the following administration schemes:

in a 3 month trial, 75 mg or 150 mg compound 37 administered perorally daily as a single dose on day 2-7 of the menstrual cycle in a 3 months trial, 75 mg, 100 mg or 150 mg compound 37 administered perorally daily as a single dose on day 2-7 of the menstrual cycle followed by a 3 months treatment-free period in a 6 months trial, 75 mg or 150 mg compound 37 administered perorally daily as a single dose 50 mg or 150 mg per compound 37 administered daily as a single dose over 42 days (6 weeks)

The treatments with compound 37 according to above doses and administration schemes demonstrate the effectiveness of the treatments of the invention, in particular in endometriosis, benign prostate hyperplasia (BPH) and prostate cancer.

The results further demonstrate that chemical (hormonal) castration can be successfully prevented.

Example 5

Study subjects are treated with compound 52 with the following doses according to the following administration schemes:

in a 3 month trial, 75 mg or 150 mg compound 52 administered perorally daily as a single dose on day 2-7 of the menstrual cycle in a 3 months trial, 75 mg, 100 mg or 150 mg compound 52 administered perorally daily as a single dose on day 2-7 of the menstrual cycle followed by a 3 months treatment-free period in a 6 months trial, 75 mg or 150 mg compound 52 administered perorally daily as a single dose 50 mg or 150 mg per compound 52 administered daily as a single dose over 42 days (6 weeks)

The treatments with compound 52 according to above doses and administration schemes demonstrate the effectiveness of the treatments of the invention, in particular in endometriosis, benign prostate hyperplasia (BPH) and prostate cancer.

The results further demonstrate that chemical (hormonal) castration can be successfully prevented.

Example 6

Study subjects are treated with compound 144 with the following doses according to the following administration schemes:

in a 3 month trial, 75 mg or 150 mg compound 144 administered perorally daily as a single dose on day 2-7 of the menstrual cycle in a 3 months trial, 75 mg, 100 mg or 150 mg compound 144 administered perorally daily as a single dose on day 2-7 of the menstrual cycle followed by a 3 months treatment-free period in a 6 months trial, 75 mg or 150 mg compound 144 administered perorally daily as a single dose 50 mg or 150 mg per compound 144 administered daily as a single dose over 42 days (6 weeks)

The treatments with compound 144 according to above doses and administration schemes demonstrate the effectiveness of the treatments of the invention, in particular in endometriosis, benign prostate hyperplasia (BPH) and prostate cancer.

The results further demonstrate that chemical (hormonal) castration can be successfully prevented.

Example 7

Study subjects are independently treated with compounds (A) to (N), respectively, with the following doses according to the following administration schemes:

in a 3 month trial, 75 mg or 150 mg compound 144 administered perorally daily as a single dose on day 2-7 of the menstrual cycle in a 3 months trial, 75 mg, 100 mg or 150 mg compound 144 administered perorally daily as a single dose on day 2-7 of the menstrual cycle followed by a 3 months treatment-free period in a 6 months trial, 75 mg or 150 mg compound 144 administered perorally daily as a single dose 50 mg or 150 mg per compound 144 administered daily as a single dose over 42 days (6 weeks)

The treatments with compounds (A) to (N) according to above doses and administration schemes demonstrate the effectiveness of the treatments of the invention, in particular in endometriosis, benign prostate hyperplasia (BPH) and prostate cancer.

The results further demonstrate that chemical (hormonal) castration can be successfully prevented.

The invention claimed is:

1. A method for treating a prostate cancer, the method comprising: administering at least one LHRH antagonist to a subject in need thereof in an amount sufficient to treat the prostate cancer and in a dose which does not cause a chemical or hormonal castration, wherein the at least one LHRH antagonist is a tetrahydrocarbazole derivative with the formula

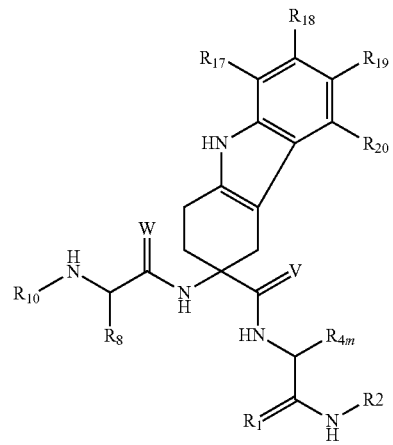

wherein V and W are each independently O, S, $S^+$—$O^-$, or geminally linked $H_2$;

$R_1$ is O, S, or $S^+$—$O^-$;

R$_2$ is an optionally substituted cycloalkyl, cycloalkylakyl, heterocyclyl, heterocyclylalkyl, heteroaryl, heteroarylalkyl, or —NHX1, wherein X1 is an optionally substituted alkyl, cycloalkyl, cycloalkylalkyl, heterocyclyl, heterocyclylalkyl, aryl, arylalkyl, heteroaryl, or heteroarylalkyl, and wherein R$_2$ or X1 is optionally substituted with —F, —Cl, —Br, —I, —CF$_3$, or —OCF$_3$;

R$_{4m}$ is an optionally substituted alkyl, cycloalkyl, cycloalkylalkyl, heterocyclyl, heterocyclylalkyl, aryl, arylalkyl, heteroaryl, or heteroarylalkyl, and wherein R$_{4m}$ is optionally substituted with —F, —Cl, —Br, —I, —CF$_3$, or —OCF$_3$;

R$_8$ is an optionally substituted alkyl, cycloalkyl, cycloalkylalkyl, heterocyclyl, heterocyclylalkyl, aryl, arylalkyl, heteroaryl, or heteroarylalkyl, and wherein R$_8$ is optionally substituted with —F, —Cl, —Br, —I, —CF$_3$, or —OCF$_3$;

R$_{10}$ is an optionally substituted alkyl, cycloalkyl, cycloalkylalkyl, heterocyclyl, heterocyclylalkyl, aryl, arylalkyl, heteroaryl, heteroarylalkyl, or —C(O)X1004, wherein X1004 is an optionally substituted cycloalkyl, heterocyclyl, aryl, arylalkyl, heteroaryl, or heteroarylalkyl, and wherein R$_{10}$ or X1004 is optionally substituted with —F, —Cl, —Br, —I, —CF$_3$, or —OCF$_3$; and R$_{17}$, R$_{18}$, R$_{19}$, and R$_{20}$ are each independently —H, —F, —Cl, —Br, —I, —CF$_3$, or —OCF$_3$.

2. The method as claimed in claim 1, wherein the at least one LHRH antagonist is a tetrahydrocarbazole derivative with the formula

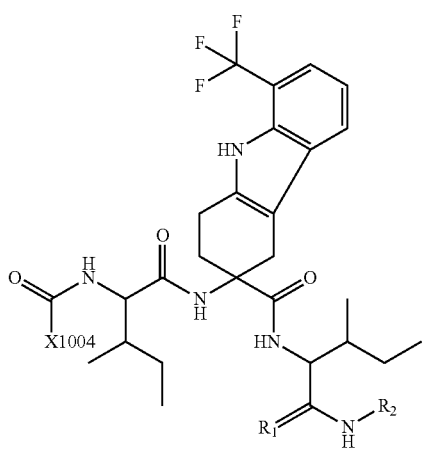

R$_1$ is O or S;
R$_2$ is heterocyclyl, heterocyclylalkyl, heteroarylalkyl, or —NHX1, wherein X1 is an aryl or heteroaryl;
X1004 is an optionally substituted aryl, arylalkyl, heteroaryl, or heteroarylalkyl, wherein X1004 is optionally substituted with —F, —Cl, —Br, or —I.

3. The method as claimed in claim 2, wherein R$_2$ is heterocyclylalkyl or —NHX1, wherein X1 is an aryl or heteroaryl; and X1004 is an optionally substituted arylalkyl or heteroarylalkyl, wherein X1004 is optionally substituted with —F, —Cl, —Br, or —I.

4. The method as claimed in claim 2, wherein R$_2$ is heterocyclylalkyl or —NHX1, wherein X1 is an aryl; and X1004 is an optionally substituted arylalkyl or heteroarylalkyl, wherein X1004 is optionally substituted with —F.

5. The method as claimed in claim 2, wherein R$_2$ is heterocyclylalkyl or —NHX1, wherein X1 is an aryl; and X1004 is an optionally substituted arylalkyl, wherein X1004 is optionally substituted with —F.

6. The method as claimed in claim 1, wherein the at least one LHRH antagonist is

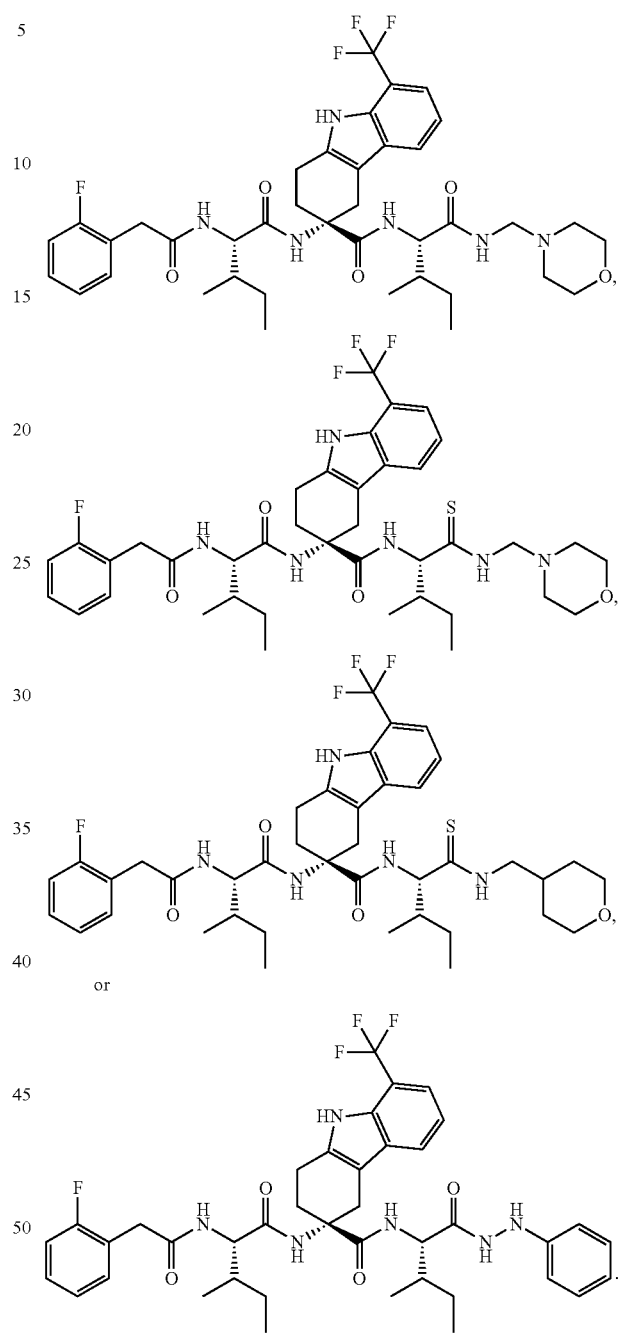

7. The method as claimed in claim 1, wherein the dose is a total monthly dose in the range of 10 mg to 150 mg of the at least one LHRH antagonist.

8. The method as claimed in claim 1, wherein the dose is a total monthly dose in the range of 10 mg to 120 mg of the at least one LHRH antagonist.

9. The method as claimed in claim 1, wherein the dose is a total monthly dose in the range of 10 mg to 40 mg of the at least one LHRH antagonist.

10. The method as claimed in claim 1, wherein the dose is a total monthly dose in the range of 40 mg to 150 mg of the at least one LHRH antagonist.

11. The method as claimed in claim 1, wherein the dose is a total monthly dose in the range of 60 mg to 150 mg of the at least one LHRH antagonist.

12. The method as claimed in claim 1, wherein the dose is a total monthly dose in the range of 60 mg to 120 mg of the at least one LHRH antagonist.

13. The method as claimed in claim 1 wherein the dose is a total monthly dose of 10 mg, 20 mg, 30 mg, 40 mg, 60 mg, 90 mg, 120 mg, 130 mg or 150 mg of the at least one LHRH antagonist.

14. The method as claimed in claim 1, wherein the total monthly dose is administered as one single monthly administration or is to be administered twice a month, three-times a month or four-times a month.

15. The method as claimed in claim 14, wherein the total monthly dose is administered biweekly.

16. The method as claimed in claim 14, wherein the total monthly dose is administered weekly.

17. The method as claimed in claim 1, wherein the dose is a single or multiple daily dose of 0.1 mg to 250 mg LHRH antagonist, wherein the single or multiple daily dose is administered over 1 day, 2 days, 3 days, 4 days, 5 days, 6 days or more days, 1 week, 2 weeks, 3 weeks, 4 weeks, 5 weeks, 6 weeks or more weeks, 1 months, 2 months, 3 months, 4 months, 5 months, 6 months or more months, wherein the administration of each single or multiple dose can be followed by a treatment-free period of 1 day, 2 days, 3 days, 4 days, 5 days, 6 days or more days, 1 week, 2 weeks, 3 weeks, 4 weeks, 5 weeks, 6 weeks or more weeks, 1 months, 2 months, 3 months, 4 months, 5 months, 6 months or more months.

18. The method as claimed in claim 1, wherein the at least one LHRH antagonist is administered over a treatment period of 1 or 2 months followed by a treatment-free period of 1, 2, 3, 4 or 5 months.

19. The method as claimed in claim 18, wherein the treatment-free period is 2 months or 5 months.

20. The method as claimed in claim 1, wherein the at least one LHRH antagonist is be administered in a dose of: 5 mg of the at least one LHRH antagonist four-times a month, three-times a month or twice a month, or 10 mg of the at least one LHRH antagonist four-times a month, three-times a month or twice a month, or 15 mg of the at least one LHRH antagonist four-times a month, three-times a month or twice a month, or 30 mg of the at least one LHRH antagonist four-times a month, three-times a month or twice a month, or 60 mg of the at least one LHRH antagonist as one single administration followed by 30 mg LHRH antagonist as one single administration two weeks later, or 60 mg of the at least one LHRH antagonist twice a month, over a treatment period of 1 or 2 months followed by a treatment-free period of 1, 2, 3, 4 or 5 months.

21. The method as claimed in claim 20, wherein the treatment-free period is 2 or 5 months.

22. The method as claimed in claim 14, wherein the treatment cycle is repeated after the end of the treatment-free period once, twice, three-times, four-times, five-times or continuously and wherein each respective succeeding treatment cycle can be identical or different to each respective preceding treatment cycle.

23. The method as claimed in claim 1, wherein the chemical or hormonal castration is a testosterone castration with a testosterone blood level of equal or below 1.2 ng/mL.

24. The method as claimed in claim 1, wherein the chemical or hormonal castration is a testosterone castration with a testosterone blood level of equal or below 0.5 ng/mL.

25. The method as claimed in claim 1, wherein the at least one LHRH antagonist is

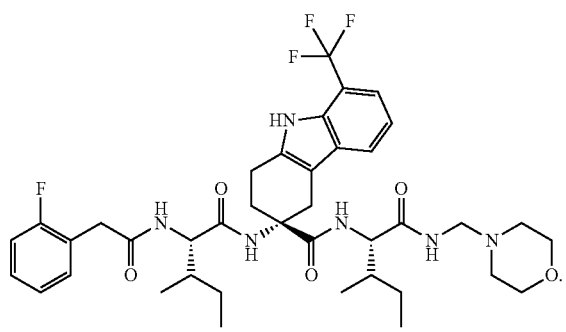

26. The method as claimed in claim 1, wherein the dose is a single or multiple daily dose of 1 mg to 60 mg LHRH antagonist, wherein the single or multiple daily dose is administered over 1 day, 2 days, 3 days, 4 days, 5 days, 6 days or more days, 1 week, 2 weeks, 3 weeks, 4 weeks, 5 weeks, 6 weeks or more weeks, 1 months, 2 months, 3 months, 4 months, 5 months, 6 months or more months, wherein the administration of each single or multiple dose can be followed by a treatment-free period of 1 day, 2 days, 3 days, 4 days, 5 days, 6 days or more days, 1 week, 2 weeks, 3 weeks, 4 weeks, 5 weeks, 6 weeks or more weeks, 1 months, 2 months, 3 months, 4 months, 5 months, 6 months or more months.

27. The method as claimed in claim 1, wherein the dose is a single or multiple daily dose of 50 mg to 150 mg LHRH antagonist, wherein the single or multiple daily dose is administered over 1 day, 2 days, 3 days, 4 days, 5 days, 6 days or more days, 1 week, 2 weeks, 3 weeks, 4 weeks, 5 weeks, 6 weeks or more weeks, 1 months, 2 months, 3 months, 4 months, 5 months, 6 months or more months, wherein the administration of each single or multiple dose can be followed by a treatment-free period of 1 day, 2 days, 3 days, 4 days, 5 days, 6 days or more days, 1 week, 2 weeks, 3 weeks, 4 weeks, 5 weeks, 6 weeks or more weeks, 1 months, 2 months, 3 months, 4 months, 5 months, 6 months or more months.

28. The method as claimed in claim 1, wherein the dose is a single or multiple daily dose of 50 mg, 75 mg or 150 mg LHRH antagonist, wherein the single or multiple daily dose is administered over 1 day, 2 days, 3 days, 4 days, 5 days, 6 days or more days, 1 week, 2 weeks, 3 weeks, 4 weeks, 5 weeks, 6 weeks or more weeks, 1 months, 2 months, 3 months, 4 months, 5 months, 6 months or more months, wherein the administration of each single or multiple dose can be followed by a treatment-free period of 1 day, 2 days, 3 days, 4 days, 5 days, 6 days or more days, 1 week, 2 weeks, 3 weeks, 4 weeks, 5 weeks, 6 weeks or more weeks, 1 months, 2 months, 3 months, 4 months, 5 months, 6 months or more months.

* * * * *